(12) United States Patent
Stringer, III et al.

(10) Patent No.: US 12,089,982 B2
(45) Date of Patent: Sep. 17, 2024

(54) CALIBRATION PHANTOM FOR RADIOTHERAPY

(71) Applicant: University of Cincinnati, Cincinnati, OH (US)

(72) Inventors: Jimmy Steele Stringer, III, Cincinnati, OH (US); Henry Spitz, Cincinnati, OH (US); Peter Sandwall, Cincinnati, OH (US); Michael Lamba, Cincinnati, OH (US); Samuel Glover, Lebanon, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 17/864,361

(22) Filed: Jul. 13, 2022

(65) Prior Publication Data

US 2023/0036916 A1    Feb. 2, 2023

Related U.S. Application Data

(60) Provisional application No. 63/221,384, filed on Jul. 13, 2021.

(51) Int. Cl.
*A61B 6/00* (2024.01)
*A61B 6/58* (2024.01)

(52) U.S. Cl.
CPC .................................. *A61B 6/583* (2013.01)

(58) Field of Classification Search
None
See application file for complete search history.

(56) References Cited

U.S. PATENT DOCUMENTS

| 5,236,363 A * | 8/1993 | Sandrik | A61B 6/583 378/18 |
| 6,674,834 B1 * | 1/2004 | Acharya | A61B 6/583 378/207 |

(Continued)

OTHER PUBLICATIONS

CIRS Tissue Simulation & Phantom Technology. 2013. Tissue Equivalent CT Dose Phantoms Model 007TE. Computer Imaging Reference Systems, Inc.

(Continued)

*Primary Examiner* — Hoon K Song
(74) *Attorney, Agent, or Firm* — Dinsmore & Shohl LLP

(57) ABSTRACT

A calibration phantom for radiometric characterization and/or radiotherapy dose calculation of a subject is provided, which includes an ellipsoid base having a primary volume defining a plurality of cylindrical voids, each of said cylindrical voids configured to receive a cylindrical insert having a diameter, wherein the ellipsoid base, the primary volume, and each of said inserts are formed from a tissue substitution material independently selected to approximate a radiological property of an anatomical feature of the subject to which the ellipsoid base, the primary volume, and each of said inserts corresponds, wherein the radiological property of the tissue substitution material, the diameter of each of said inserts, and a location of each of said inserts within the ellipsoid base are selected to mimic beam hardening upon exposure of the calibration phantom to a radiation beam. Optionally, one or more peripheral rings are disposed concentrically about the ellipsoid base. Methods of mitigating off-target radiation exposure improving certainty of a radiotherapeutic dose delivered to a human subject using the calibration phantom are also provided.

18 Claims, 28 Drawing Sheets

(56) References Cited

U.S. PATENT DOCUMENTS

| | | | |
|---|---|---|---|
| 8,480,407 B2 | 7/2013 | Campbell et al. | |
| 2015/0327834 A1* | 11/2015 | Hoshino | A61B 6/484 |
| | | | 378/207 |
| 2016/0015356 A1* | 1/2016 | Baiu | G09B 23/286 |
| | | | 378/207 |

OTHER PUBLICATIONS

CIRS Tissue Simulation & Phantom Technology. 2014. 3D Sectional Torso Phantom Model 600. Computer Imaging Reference Systems, Inc.

De Matos et al. CT images of an Anthropomorphic and Anthropometric Male Pelvis Phantom. 2009 international Nuclear Atlantic Conference—INAC 2009.

Innes et al. The dependence of computed tomography number to relative electron density conversion on phantom geometry and its impact on planned dose. Australasian College of Physical Scientists and Engineers in Medicine 2014.

* cited by examiner

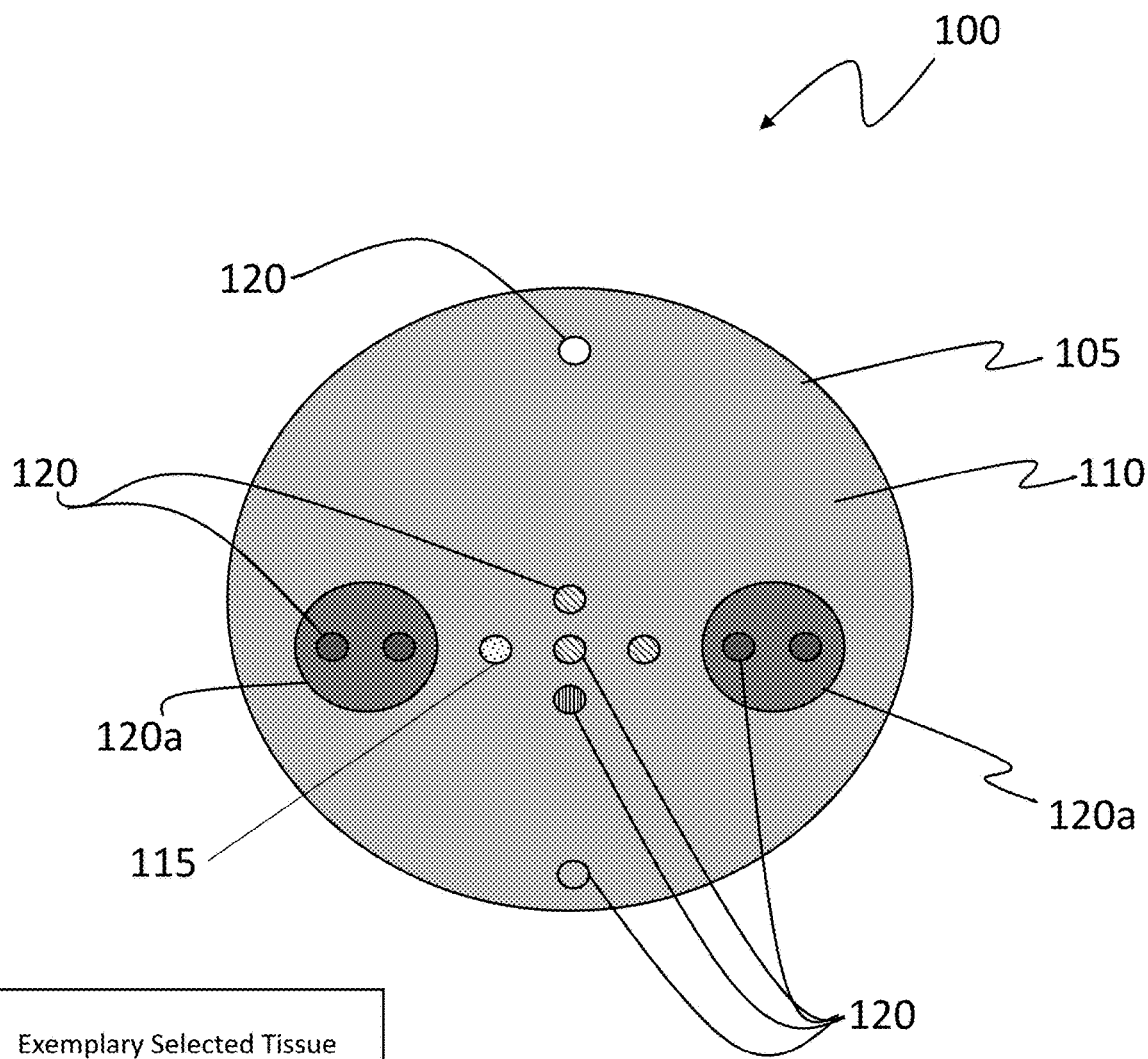
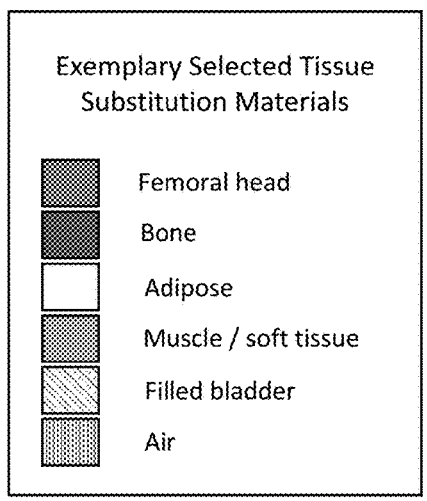
FIG. 1

Nominal Electron/Physical Densities of Rod Materials

| Rod Materials | Electron Density Relative to Water | Physical Density (g/cm$^3$) | GAMMEX Model Numbers |
|---|---|---|---|
| LN-300 Lung | 0.29 | 0.30 | 455 |
| LN-450 Lung | 0.44 | 0.45 | 485 |
| AP6 Adipose | 0.93 | 0.94 | 453 |
| BR-12 Breast | 0.96 | 0.98 | 454 |
| CT Solid Water | 0.99 | 1.02 | 451 |
| BRN-SR2 Brain | 1.04 | 1.05 | 481 |
| LV1 Liver | 1.06 | 1.10 | 482 |
| IB Inner Bone | 1.09 | 1.14 | 456 |
| B200 Bone Mineral | 1.10 | 1.15 | 487 |
| CB2 – 30% CaCO$_3$ | 1.28 | 1.34 | 484 |
| CB2 – 50% CaCO$_3$ | 1.47 | 1.56 | 480 |
| SB3 Cortical bone (Optional) | 1.69 | 1.82 | 450 |
| Titanium Insert Rod | 3.79 | 4.59 | N/A |
| Muscle | 1.02 | 1.05 | 452 |

FIG. 6

| Uncertainty source | Uncertainties in SPR Estimation (1σ) | | |
|---|---|---|---|
| | Lung (%) | Soft (%) | Bone (%) |
| Uncertainties in patient CT imaging | 3.3 | 0.6 | 1.5 |
| Uncertainties in the parameterized stoichiometric formula to calculate theoretical CT numbers | 3.8 | 0.8 | 0.5 |
| Uncertainties due to deviation of actual human body tissue from ICRU standard tissue | 0.2 | 1.2 | 1.6 |
| Uncertainties in mean excitation energies | 0.2 | 0.2 | 0.6 |
| Uncertainties due to energy dependence of SPR not accounted by dose algorithm | 0.2 | 0.2 | 0.4 |
| Total (root-sum-square) | 5.0 | 1.6 | 2.4 |

FIG. 8

| Tumor Site | Composite Range Uncertainty | | | Percentile when range uncertainty = 3.5% |
|---|---|---|---|---|
| | Median | 90th Percentile | 95th Percentile | |
| Prostate | 1.3 | 2.5 | 3.0 | 98% |
| Lung | 1.5 | 2.9 | 3.4 | 96% |
| Head and neck | 1.3 | 2.6 | 3.0 | 98% |

FIG. 9

| Component | Purpose | Density (g/cm$^3$) |
|---|---|---|
| LHT – 240 | Base compound for tissue equivalent material | 1.04 |
| Stannous Octoate | Catalyst | 1.251 |
| SAG – 471 | Used to control foaming during chemical reaction | 0.993 |
| Adiprene | Base compound for tissue equivalent material | 1.04 |
| Calcium Carbonate | Additive that increases the effective Z of the base compound for the tissue equivalent material | 2.71 |

FIG. 10

| Energy (keV) | Ratio of Photo Electric to Total Attenuation: Adipose |
|---|---|
| 30 to 40 | 0.250 |
| 40 to 50 | 0.140 |
| 50 to 60 | 0.050 |
| 60 to 70 | 0.040 |
| 70 to 80 | 0.024 |
| 80 to 90 | 0.020 |
| 90 to 100 | 0.011 |
| 100 to 110 | 0.008 |
| 110 to 120 | 0.006 |

| Energy (keV) | Ratio of Photo Electric to Total Attenuation: Muscle |
|---|---|
| 30 to 40 | 0.399 |
| 40 to 50 | 0.221 |
| 50 to 60 | 0.127 |
| 60 to 70 | 0.077 |
| 70 to 80 | 0.050 |
| 80 to 90 | 0.034 |
| 90 to 100 | 0.017 |
| 100 to 110 | 0.017 |
| 110 to 120 | 0.013 |

| Energy (keV) | Ratio of Photo Electric to Total Attenuation: Femur |
|---|---|
| 30 to 40 | 0.730 |
| 40 to 50 | 0.550 |
| 50 to 60 | 0.398 |
| 60 to 70 | 0.284 |
| 70 to 80 | 0.200 |
| 80 to 90 | 0.148 |
| 90 to 100 | 0.105 |
| 100 to 110 | 0.083 |
| 110 to 120 | 0.063 |

| Energy (keV) | Ratio of Photo Electric to Total Attenuation: Prostate |
|---|---|
| 30 to 40 | 0.37 |
| 40 to 50 | 0.20 |
| 50 to 60 | 0.11 |
| 60 to 70 | 0.07 |
| 70 to 80 | 0.04 |
| 80 to 90 | 0.03 |
| 90 to 100 | 0.02 |
| 100 to 110 | 0.02 |
| 110 to 120 | 0.01 |

| Energy Range (keV) | Relative Contribution to Total Spectrum |
|---|---|
| 30 to 40 | 5.64% |
| 40 to 50 | 13.67% |
| 50 to 60 | 26.33% |
| 60 to 70 | 18.42% |
| 70 to 80 | 12.30% |
| 80 to 90 | 9.75% |
| 90 to 100 | 7.17% |
| 100 to 110 | 4.68% |
| 110 to 120 | 2.04% |

| Tissue Attenuators | Average Energy (keV) |
|---|---|
| None | 66.3 |
| Adipose (3 cm) | 67.3 |
| Adipose-> Muscle (13 cm) | 74.2 |

| Energy Range (keV) | Relative Contribution to Total Spectrum at the Prostate for Path A |
|---|---|
| 30 to 40 | 1.09% |
| 40 to 50 | 6.97% |
| 50 to 60 | 22.24% |
| 60 to 70 | 20.08% |
| 70 to 80 | 15.77% |
| 80 to 90 | 14.25% |
| 90 to 100 | 11.72% |
| 100 to 110 | 8.40% |
| 110 to 120 | 3.83% |

| Tissue Attenuators | Average Energy (keV) |
|---|---|
| None | 66.3 |
| Adipose | 67.3 |
| Adipose-> Muscle | 70.7 |
| Adipose-> Muscle-> Bone | 79.5 |
| Adipose-> Muscle-> Bone-> Muscle | 81.8 |

| Energy Range (keV) | Relative Contribution to Total Spectrum at the Prostate for Path B |
|---|---|
| 30 to 40 | 0.01% |
| 40 to 50 | 0.99% |
| 50 to 60 | 13.15% |
| 60 to 70 | 18.58% |
| 70 to 80 | 18.20% |
| 80 to 90 | 17.34% |
| 90 to 100 | 17.42% |
| 100 to 110 | 13.17% |
| 110 to 120 | 6.47% |

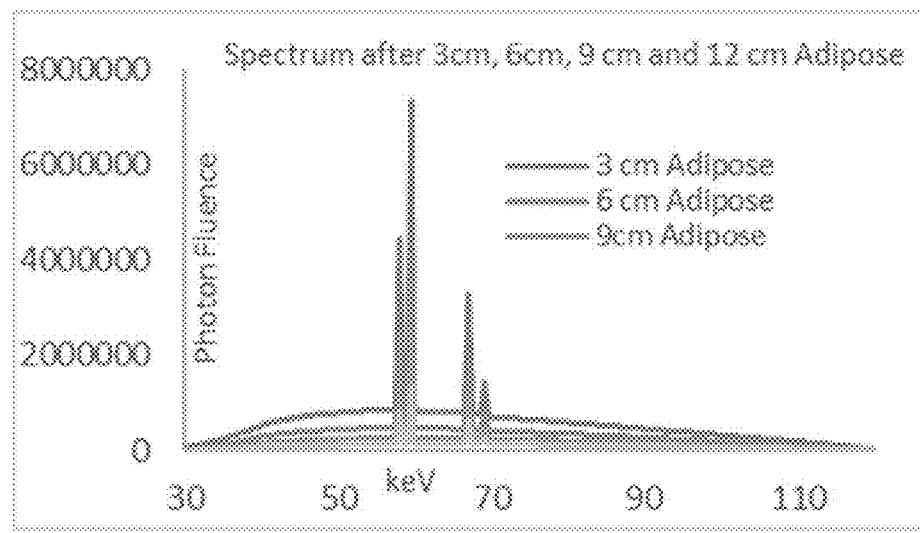
FIG. 37
| Adipose Thickness | Average Energy (keV) |
|---|---|
| 3 cm | 67 |
| 6 cm | 68.2 |
| 9 cm | 69.3 |
| 12 cm | 69.8 |
FIG. 38
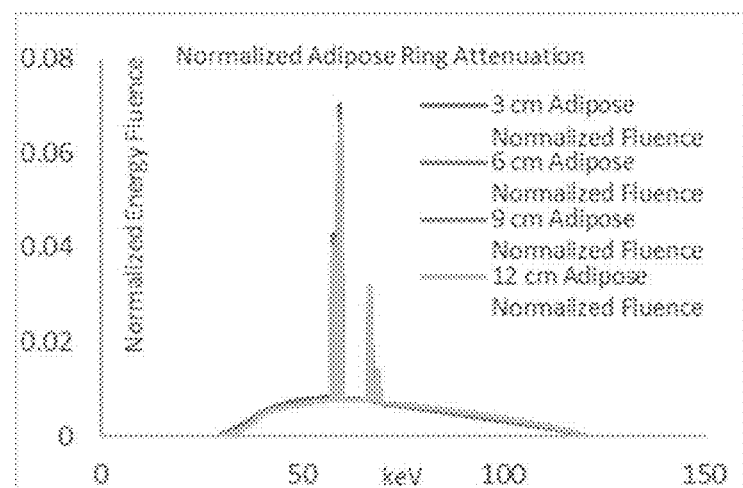
FIG. 39

| 3cm material | Average Energy (keV) |
|---|---|
| New Phantom Adipose | 67.29 |
| Gammex Water equivalent | 67.13 |

| Femoral Head Attenuation | Average Energy (keV) |
|---|---|
| New Phantom | 77.25 |
| Gammex | 72.3 |

CALIBRATION PHANTOM FOR RADIOTHERAPY

CROSS-REFERENCE TO RELATED APPLICATIONS

This application claims priority to U.S. Application Ser. No. 63/221,384, filed Jul. 13, 2021, the entire contents of which are incorporated herein by reference.

TECHNICAL FIELD

The present disclosure pertains to the field of radiotherapy and radiometric imaging. Specifically, the present disclosure relates to an improved calibration phantom that reflects patient anthropomorphic and anthropometric characteristics, for use in radiotherapy and radiometric imaging.

BACKGROUND

Some forms of cancer treatment take advantage of the sensitivity of cancer cells to damage by radiation. Radiation-generating machines can produce a beam of x-rays that can be directed toward a localized cancer tumor in an organ or tissue inside the body. Another type of radiation-generating machine can produce a beam of protons that has the advantage of sparing more healthy, non-cancerous tissue than a beam of x-rays while delivering a therapeutic radiation dose to the tumor. In either type of treatment, a computerized tomographic (CT) x-ray image of the body is obtained in order to locate the tumor and determine the type of tissue through which the x-ray or proton beam must penetrate to reach the cancerous tumor. Data provided by the CT image (reported as Hounsfield Units) can be converted into a quantity that describes the radiation absorption quality (i.e., electron density) of each type of tissue exposed to the beam. Conversion of Hounsfield Units (HU) to electron density (ED) is determined by separately measuring a calibration structure (i.e., a phantom) that exhibits the same chemical, physical, and radiological properties as the human body. Conventional phantoms are designed to simulate the tissue in an average adult and do not reflect recognized differences in these properties based on race, sex, age, and patient health status. Furthermore, conventional phantoms do not reflect how the energy distribution in the radiation beam changes as it penetrates the body. This change in energy distribution is referred to as beam hardening and distorts Hounsfield Unit values in the CT image obtained for treatment planning.

One of the major limiting factors that prevents full optimization of proton radiotherapy is the uncertainty in determining exactly where the maximum proton energy is located, i.e., the proton range. Although Bragg Theory can predict the range of a proton of specific energy, determining the range of a beam of protons penetrating many layers of different types of tissue can be uncertain. Beam hardening is a significant contributor to range uncertainty in proton radiotherapy and is due to variations in the attenuation of low energy photons due to the differences in radiometric properties between patient anatomy and the conventional calibration phantoms.

A need exists for improved calibration phantoms that more closely approximate patient anthropomorphic and anthropometric characteristics, thereby facilitating more accurate imaging and radiotherapy dosimetry.

SUMMARY

Accordingly, provided herein is a calibration phantom for use in radiometric characterization and/or proton beam or conventional external radiation dose calculation, the calibration phantom comprising an arrangement of elements formed from materials that mimic the anthropomorphic and anthropometric characteristics of a subject's anatomy, such as a human subject. Advantageously, the disclosed calibration phantom is capable of modeling beam hardening of a radiation beam, thereby providing more accurate radiometric data for use in determining radiation dose.

In one embodiment, calibration phantom for radiometric characterization and/or radiotherapy dose calculation of a subject is provided, comprising: an ellipsoid base having a primary volume defining a plurality of cylindrical voids, each of said cylindrical voids configured to receive a cylindrical insert having a diameter, wherein the ellipsoid base, the primary volume, and each of said inserts are formed from a tissue substitution material independently selected to approximate a radiological property of an anatomical feature of the subject to which the ellipsoid base, the primary volume, and each of said inserts corresponds, wherein the radiological property of the tissue substitution material, the diameter of each of said inserts, and a location of each of said inserts within the ellipsoid base are selected to mimic beam hardening upon exposure of the calibration phantom to a radiation beam.

In another embodiment, the calibration phantom further comprises one or more peripheral rings disposed concentrically about the ellipsoid base, wherein the one or more peripheral rings are formed from a tissue substitution material independently selected to approximate a radiological property of an anatomical feature of the subject to which the one or more peripheral rings correspond.

In another embodiment, a method of mitigating off-target exposure to radiotherapy in a subject in need thereof is provided, the method comprising calibrating a radiation-generating therapeutic device using a calibration phantom according to the present disclosure, prior to administering the radiotherapy to the patient.

In another embodiment, a method of improving certainty of a radiotherapeutic dose delivered to a human subject is provided, the method comprising calibrating a radiation-generating therapeutic device using a calibration phantom according the present disclosure, prior to administering the radiotherapeutic dose to the human subject.

These and other objects, features, embodiments, and advantages will become apparent to those of ordinary skill in the art from a reading of the following detailed description and the appended claims.

BRIEF DESCRIPTION OF THE DRAWINGS

FIG. 1 is an illustration of a transverse cross sectional view of a prostate calibration phantom according to one or more embodiments of the present disclosure.

FIG. 6 is a table of nominal electron/physical densities of exemplary rod materials.

FIG. 8 is a table of estimates of uncertainties (1σ) in patient stopping-power-ratio (SPR) estimation in current clinical practice, reproduced from Yang, et al., *Comprehensive analysis of proton range uncertainties related to patient stopping-power-ratio estimation using the stoichiometric calibration*, Phys Med Biol 57(13):4095-115 (2012).

FIG. 9 is a table of median, 90th percentile and 95th percentile of composite range uncertainties and the corresponding percentile when the range uncertainty is 3.5% at different clinical sites, reproduced from Yang, et al. (2012).

FIG. 10 is a table of the constituents of an exemplary tissue equivalent material according to one or more embodiments of the present disclosure.

FIG. 37 is a graph showing the impact of adipose thickness on the relationship between energy and photon fluence.

FIG. 38 is a table showing average energy (keV) at differing adipose thicknesses.

FIG. 39 is a graph showing normalized adipose ring attenuation at differing adipose thicknesses.

DETAILED DESCRIPTION

Figure 2:
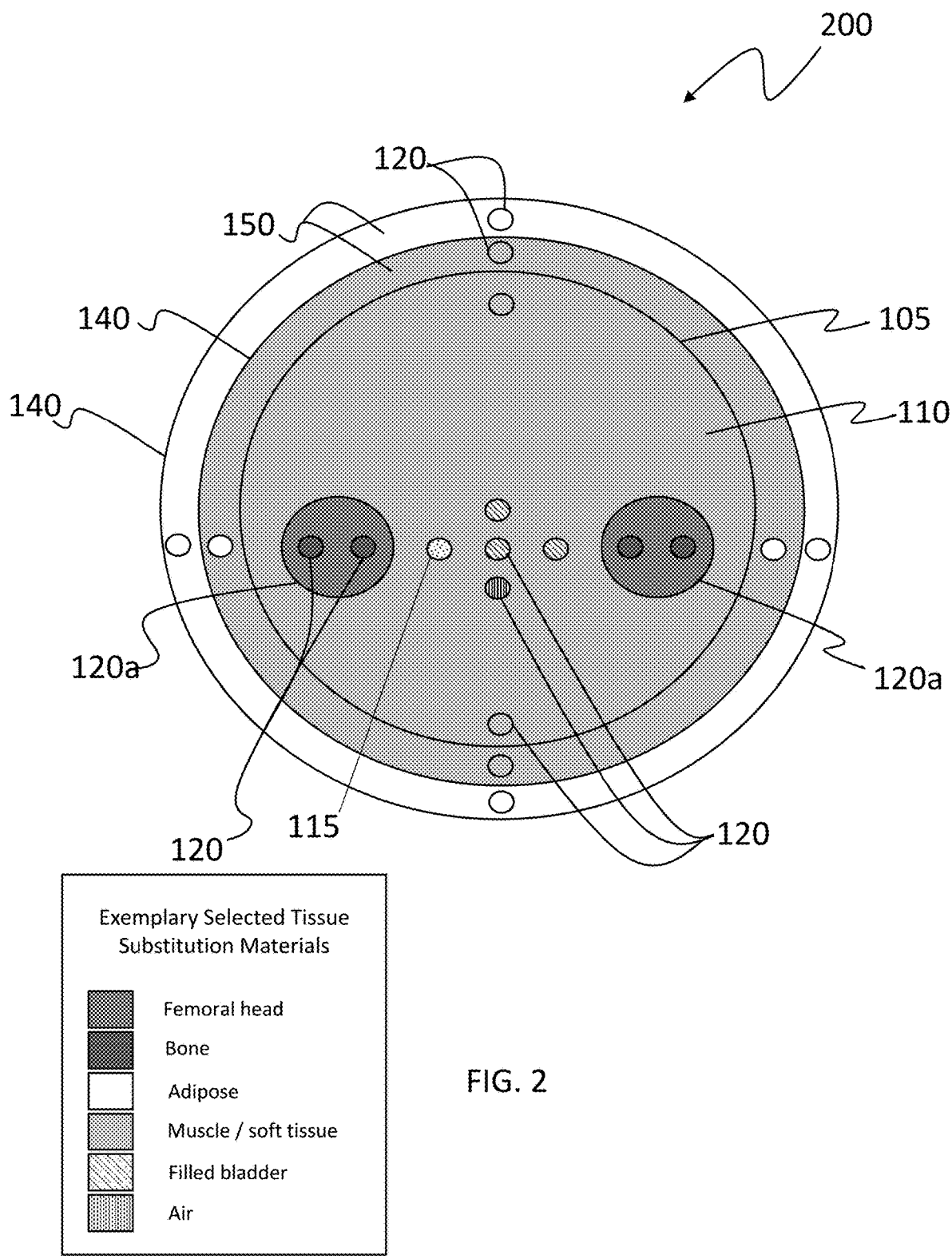
FIG. 2 is an illustration of a transverse cross sectional view of an embodiment of a prostate calibration phantom according to one or more embodiments of the present disclosure showing the concentric cylinders of the phantom.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless otherwise defined, all terms (including technical and scientific terms) used herein have the same meaning as commonly understood by one of ordinary skill in the art to which this disclosure belongs. It will be further understood that terms such as those defined in commonly used dictionaries should be interpreted as having a meaning that is consistent with their meaning in the context of the relevant art and the present disclosure, and will not be interpreted in an idealized or overly formal sense unless expressly so defined herein.

As used herein, "radiometric" characterization includes radiometric imaging, such as CT scanning, x-ray imaging, and the like.

As used herein, "radiotherapy" refers to radiation therapy employed, for example, as part of a cancer treatment to kill or control cancer cells in a subject. Radiotherapy damages DNA by applying energy to a cell in the form of photons or charged particles. Exemplary radiotherapy methods include photon therapy, or conventional external beam radiation, as well as charged particle radiation, e.g., delivery of charged particles such as protons, boron, carbon, and neon. In specific embodiments, the radiotherapy is proton beam therapy.

"Radiological property," as used herein, refers to a property of a material that influences the interaction of that material with radiation, e.g., photons and/or charged particles. In embodiments, the radiological property is a radiometric property, i.e., capable of measurement. In a specific embodiment, the radiological property is selected from the group consisting of density, electron density, mass attenuation coefficient, linear attenuation coefficient, stopping power, and combinations thereof.

"Anthropomorphic," as used herein, refers to a physical resemblance to a human body. For example, the calibration phantoms described herein are designed to mimic, approximate, or resemble, via their geometry and selected composition materials, a human body or a portion thereof, such as a head, neck, torso, chest, arm, leg, or pelvis thereof.

"Anthropometric," as used herein, refers to measurable characteristics that approximate the measurable characteristics of a human body or a portion thereof, such as a head, neck, torso, chest, arm, leg, or pelvis thereof. For example, the calibration phantoms described herein are designed to mimic, approximate, or resemble, via their measurable radiological properties, the measurable radiological properties of a human body or a portion thereof.

The present disclosure relates to a phantom that reflects actual patient anthropomorphic and/or anthropometric characteristics to achieve a more reliable measure of Hounsfield Unit (HU) to electron density (ED) calibration curves, leading to higher certainty in the calculation of delivered dose to a tumor. The design of the calibration phantom reflects actual patient anthropometric characteristics to achieve a more reliable measure of radiation interactions and to reduce the uncertainty in the HU to ED calibration measurements. The basic design of a phantom according to the present disclosure is shown in FIG. 1 and includes inserts formed from tissue substitute materials for soft tissue, water, bone, and other materials of known electron density.

Referring to FIG. 1, a cross-section of an exemplary calibration phantom 100 according to the present disclosure is provided. The calibration phantom 100 comprises an ellipsoid base 105 comprising a primary volume 110. While an ellipsoidal embodiment is illustrated, it will be readily appreciated that the cross-sectional shape of the ellipsoid base 105 may be substantially circular, ellipsoidal, or otherwise configured to approximate the cross-sectional dimensions of a subject. For example, as depicted in FIG. 1 the ellipsoid base is representative of the epidermis surrounding a transverse cross-section of a subject. As seen in FIG. 2, the overall diameter of the phantom can be adjusted with additional peripheral rings to accommodate fluctuations in a subject's body type.

The primary volume 110 is comprised of a material, such as a tissue substitution material, which defines a plurality of cylindrical voids 115, each of which is configured to receive a cylindrical insert 120 or 120a. In embodiments, one or more inserts can represent larger and/or permanent structures expected within the subject's corresponding transverse cross-sectional area. For example, as depicted in FIG. 1, which is representative of a pelvic transverse cross-sectional phantom, inserts 120a corresponding to the head of the femoral bones can comprise a relatively larger diameter as compared to other cylindrical inserts, and can be positioned within the ellipsoid base 105 to approximate the diameter and location of femoral heads within a cross-section of a corresponding human subject. It should also be appreciated that the diameter, perimeter, as well as overall shape of any insert 120 can be subject to change, as can the placement and number within the ellipsoid base 105 depending on the region within the subject for which the phantom is to correlate. For example, in some embodiments, an insert may not be required, whereas in others a greater or fewer number of inserts may be required than those illustrated in FIG. 1. Those skilled in the art will appreciate that number, placement/location, and diameter of inserts 120 are dependent on the anatomy the phantom is mimicking or representing.

In embodiments, the inserts 120, 120a are removable cylindrical inserts that "plug" into the voids 115 of the ellipsoid base 105. In other embodiments, the inserts 120 are integrated permanently or semi-permanently into the ellipsoid base 105. In a very specific embodiment, the calibration phantom is a transverse cross-sectional model of a human pelvis and the inserts 120a are formed of tissue substitute materials selected to mimic the anthropomorphic and anthropometric characteristics of the human femoral head tissue, e.g., bone.

The inserts 120 are optionally formed from a tissue substitute material or a material with one or more physical characteristics representative of a corresponding tissue and/ or organ in a corresponding transverse cross-section of a subject. In specific embodiments, the tissue substitute material of each insert 120 is independently selected and the insert 120 is sized to approximate the radiological properties of an internal tissue and/or organ of the human body, such as lung, breast, liver, brain, bone, thyroid, bladder, prostate, rectum, water, air, adipose, muscle, and the like. In embodiments, an insert 120 may be optionally configured to receive one or more further inserts 120. In some embodiments, the diameter of the inserts 120 may be varied depending on the tissue and/or organ it is intended to mimic. It will also be appreciated that inserts having a uniform cross-sectional diameter and/or shape can be interchanged within the ellipsoid base 105 of the phantom 100 in general, expanding the flexibility and use thereof. In a more specific embodiment, inserts 120*a* are designed to mimic the human femoral head and are configured to receive inserts 120 that mimic human bone.

The phantom design includes features that accommodate for varying body types and physiques between different subjects through the addition of one or more peripheral rings. FIG. 2 illustrates the concentric nature of an exemplary calibration phantom 200, wherein additional peripheral rings 140 compensate for corresponding patient morphology.

Referring to FIG. 2 and continuing with the example of a transverse cross-section of a subject's pelvis, the exemplary calibration phantom 200 comprises a central ellipsoid base 105 comprising a primary volume 110. The primary volume 110 is comprised of a material, such as a tissue substitution material, which defines a plurality of cylindrical voids 115, each of which is configured to receive a cylindrical insert 120 or 120*a*.

In embodiments, one or more inserts can represent larger and/or permanent structures expected within the subject's corresponding transverse cross-sectional area. For example, as depicted in FIG. 2, which is representative of a pelvic transverse cross-section, inserts 120*a* corresponding to the head of the femoral bones can comprise a relatively larger diameter than other cylindrical inserts, and can be positioned within the ellipsoid base 105 to approximate the location of femoral heads within a cross-section of a human subject. It should also be appreciated that the diameter, perimeter, as well as overall shape of any insert 120 can be subject to change, as can the placement and number within the ellipsoid base 105 depending on the region within the subject for which the phantom is to correlate. For example, in some embodiments, an insert may not be required, whereas in others a greater or fewer number of inserts may be required than those illustrated in FIG. 2. Those skilled in the art will appreciate that number, location, and diameter of inserts 120, 120*a* are dependent on the anatomy the phantom is mimicking or representing. In embodiments, the inserts are removable cylindrical inserts that "plug" into the voids 115 of the ellipsoid base 105. In other embodiments, the inserts 120 are integrated permanently or semi-permanently into the ellipsoid base 105. In a very specific embodiment, the calibration phantom is a transverse cross-sectional model of a human pelvis and the inserts 120*a* are formed of tissue substitute materials selected to mimic the anthropomorphic and anthropometric characteristics of the human femoral head, e.g., bone.

Still referring to FIG. 2, the inserts 120 are optionally formed from a tissue substitute material or a material with one or more physical characteristics representative of a corresponding tissue and/or organ in a corresponding transverse cross-section of a subject. In specific embodiments, the tissue substitute material of each insert 120 is independently selected and each insert 120 is sized to approximate the radiological properties of an internal tissue and/or organ of the human body, such as lung, breast, liver, brain, bone, thyroid, prostate, rectum, bladder, water, air, adipose, muscle, and the like. In embodiments, an insert 120 may be optionally configured to receive one or more additional inserts 120. In some embodiments, the diameter and/or cross-sectional shape of the inserts 120 may be varied depending on the tissue and/or organ it is intended to mimic. It will also be appreciated that inserts having a uniform cross-sectional diameter and/or shape can be interchanged within the ellipsoid base 105 of the phantom 200 in general, expanding the flexibility and use thereof. In a more specific embodiment, inserts 120*a* are designed to mimic the human femoral head and are configured to receive inserts 120 that mimic human bone.

Still referring to FIG. 2, the phantom design includes features that accommodate for varying body types and physiques between different subjects through the addition of one or more peripheral rings 140. FIG. 2 illustrates the concentric nature of an exemplary calibration phantom 200, whereby additional peripheral rings 140 compensate for patient morphology.

The phantom 200 further comprises one or more peripheral rings 140, each comprising a peripheral volume 150. In embodiments, the peripheral rings 140 and the peripheral volumes 150 are formed from a tissue substitute material independently selected to approximate a desired tissue of the human body, such as lung, breast, liver, brain, bone, thyroid, prostate, rectum, bladder, water, air, adipose, muscle, and the like. In specific embodiments, a peripheral ring 140 is comprised of a tissue substitute material selected to approximate muscle or adipose tissue. The peripheral volume 150 of a peripheral ring 140 may define one or more cylindrical voids 115, each of said cylindrical voids 115 configured to receive a cylindrical insert 120, wherein each of said inserts 120 is formed from a tissue substitution material independently selected to approximate a radiological property of an anatomical feature of the subject to which each of said inserts 120 corresponds. In a very specific embodiment, inserts 120 of the peripheral rings 140 are formed from a tissue substitute material that approximates muscle or adipose tissue.

It will be appreciated that the presence of a second peripheral ring 140 is not necessarily required to accompany a first peripheral ring 140. The skilled person will appreciate that additional concentric peripheral rings 140 may be added, such as a third, fourth, fifth, sixth, and so on peripheral ring 140, in order to achieve a calibration phantom that best approximates the weight, dimensions, and/or anatomy of a specific subject. Optionally, a second peripheral ring 140 and any subsequent peripheral ring may be configured to receive one or more inserts 120, thereby allowing for more accurate placement of the tissue and/or organ that it is employed to mimic and/or represent.

In some embodiments, inserts 120 are interchangeable and may be moved from a position within the ellipsoid base 105 to a peripheral ring 140 to better represent the particular subject at hand.

Figure 45:
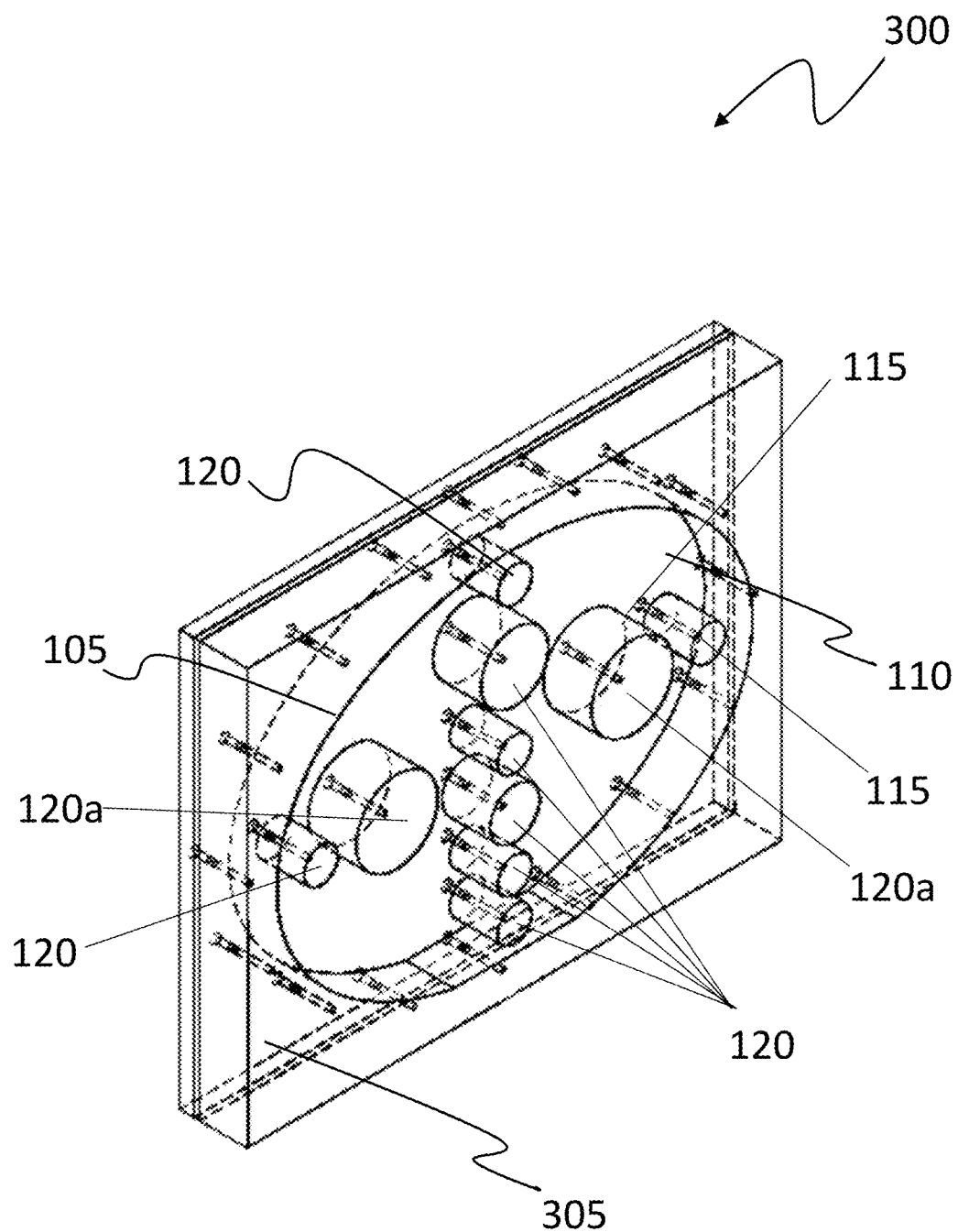
FIG. 45 is a perspective view of a calibration phantom, according to one or more embodiments of the disclosure.

Referring to FIG. 45, and continuing with the example of a transverse cross-section of a subject's pelvis, the exemplary calibration phantom 300 comprises an ellipsoid base 105 comprising a primary volume 110. It is noted that FIG. 45 depicts the exemplary phantom within a manufacturing base 305, which does not form part of the phantom and is removed during the manufacturing process.

While an ellipsoidal embodiment is illustrated, it will be readily appreciated that the cross-sectional shape of the ellipsoid base 105 may be substantially circular, ellipsoidal, or otherwise configured to approximate the cross-sectional dimensions of a subject. For example, as depicted in FIG. 45 the ellipsoid base is representative of the epidermis surrounding a transverse cross-section of a subject. As seen in FIG. 2, the overall diameter of the phantom 300 can be adjusted with additional peripheral rings to accommodate fluctuations in a subject's body type. The primary volume 110 is comprised of a material, such as a tissue substitution material, which defines a plurality of cylindrical voids 115, each of which is configured to receive a cylindrical insert 120 or 120a. In embodiments, one or more inserts can represent larger and/or permanent structures expected within the subject's corresponding transverse cross-sectional area. For example, as depicted in FIG. 45, which is representative of a pelvic transverse cross-section, inserts 120a corresponding to the head of the femoral bones can comprise a relatively larger diameter than other cylindrical inserts, and can be positioned within the ellipsoid base 105 to approximate the location of femoral heads within a cross-section of a human subject. It should also be appreciated that the diameter, perimeter, as well as overall shape of any insert 120, 120a can be subject to change, as can the placement and number within the ellipsoid base 105 depending on the region within the subject for which the phantom is to correlate. For example, in some embodiments, an insert may not be required, whereas in other embodiments a greater or fewer number of inserts 120 may be required than those illustrated in FIG. 45. Those skilled in the art will appreciate that number, location, and diameter of inserts 120 are dependent on the anatomy the phantom is mimicking or representing. In embodiments, the inserts 120 are removable and can "plug" into the voids 115 of the ellipsoid base 105. In other embodiments, the inserts 120 are integrated permanently or semi-permanently into the ellipsoid base 105. In a very specific embodiment, the calibration phantom is a transverse cross-sectional model of a human pelvis and the inserts 120a are formed of tissue substitute materials selected to mimic the anthropomorphic/anthropometric characteristics of the human femoral head, e.g., bone.

The inserts 120 are optionally formed from a tissue substitute material or a material with one or more physical characteristics representative of a corresponding tissue and/or organ in a corresponding transverse cross-section of a subject. In specific embodiments, the tissue substitute material of each insert 120 is independently selected and the insert 120 is sized to approximate the radiological properties of an internal tissue and/or organ of the human body, such as lung, breast, liver, brain, bone, thyroid, water, air, adipose, and muscle. In embodiments, an insert 120 or 120a may be optionally configured to receive one or more additional inserts 120 (see FIGS. 1-2). In some embodiments, the diameter and/or cross-sectional shape of the inserts 120, 120a may be varied depending on the tissue and/or organ it is intended to mimic. It will also be appreciated that inserts having a uniform cross-sectional diameter and/or shape can be interchanged within the ellipsoid base 105 of the phantom 300 in general, expanding the flexibility and use thereof. In a more specific embodiment, inserts 120a are designed to mimic the human femoral head.

The phantom design includes features that accommodate for varying body types and physiques between different subjects through the addition of one or more peripheral rings. FIG. 2 illustrates the concentric nature of an exemplary calibration phantom 200, whereby additional peripheral rings 140 compensate for patient thickness. The calibration phantom of FIG. 300 may optionally comprise said one or more peripheral rings, as described above.

In embodiments, the present disclosure demonstrates the unique feature of the inclusion of anatomy-specific morphology using realistic tissue substitutes that provides the ability to determine beam hardening, the factor that increases uncertainty in determining proton dose to the body.

In one embodiment of the present invention, a digital image is generated by performing a computerized tomographic (CT) scan of the phantom. Regions of interest (ROI) in the scan are selected for calculating the electron density (ED) to Hounsfield Unit (HU) calibration factor using an empirical or stoichiometric method. ED-HU calibration factors are determined using the type of phantom that best reflects the patient conditions. The presently disclosed phantoms are customizable to better approximate a patient, through the selection of tissue substitution materials, the geometry of the phantom, and the optional addition of peripheral ring(s) to match a patient's physical stature.

In another embodiment, the phantom of present invention is fabricated using various formulations of polyurethanes that exhibit the radiological and chemical properties of the human tissues included in the anatomical structure. Precise quantities of additives, e.g., $CaCO_3$, $KCl$, and $NaCl$, are added to the polyurethanes to create a material that exhibits the desired radiological properties. These quantities are determined using models based on the Basic Data Method and Direct Z Effective Method, described herein.

Radiation Therapy

Radiation Oncology utilizes accurate and precise delivery of high doses of radiation to treat cancer. Determining the dose delivered for treatment through treatment planning is essential to acceptable patient outcomes. Modern treatment planning and dose determination require the ability to appropriately predict the radiation dose distribution within the patient, with an overall goal of targeting diseased tissue with high doses of radiation while sparing healthy tissue. Treatment Planning Systems (TPS) do this via Monte Carlo (MC) simulation, convolution, and analytical methods. These methods require discretization, digitization, segmentation, and radiometric characterization (cross sectional, electron density, and stopping power) of patient imaging data. The use of computed tomography (CT) has been the standard for patient imaging and characterization within radiation oncology for patient treatment planning since the early 1980s. CT imaging data is advantageous because it allows for full patient discretization, digitization, segmentation, and radiometric characterization (cross section, electron density, and stopping power) in one scan. The treatment planning system correlates the relationship between CT numbers and electron density for various tissues to predict dose in view of tissue heterogeneity. The process of correlating CT numbers to electron density is ubiquitous for most radiation therapy treatment modalities. Proton radiotherapy requires that the determined electron density values be converted into stopping power.

Proton Radiation Therapy

Proton beam radiation therapy is motivated by the need to spare dose to healthy tissue, eliminate exit dose, minimize entrance dose, and minimize integral dose. Proton radiotherapy achieves these objectives by virtue of the Bragg peak in which the proton deposits most of its energy into the target. Ideally, proton radiotherapy limits the dose to tissues that are proximal and distal to the target volume. However, uncertainties associated with patient setup, patient motion, and dosimetry to healthy tissue should be considered to ensure the target is effectively dosed.

Figure 3:
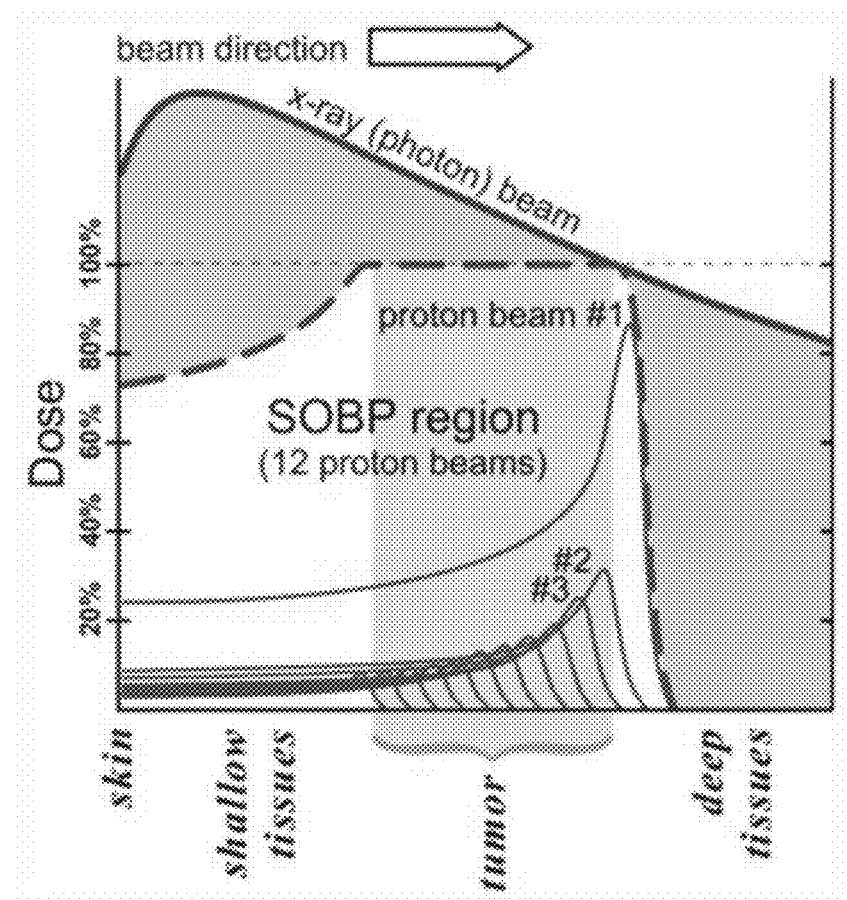
FIG. 3 is a graph illustrating the comparison between photon and proton radiotherapy dose deposition.

Dose deposition is an integral concept in recognizing the benefit of proton radiation therapy. As a result of photon exponential energy deposition, 100% of the dose is deposited in healthy tissue both proximal and distal to the target. The attenuated radiation beam has an exponential dependence on the product of the attenuation coefficient and the thickness traversed by the radiation beam, viz., e-x. On the other hand, energy transfer for charged particles is directly proportional to particle mass, energy, and material properties. The linear energy transfer (LET) of the charged particle is characterized by the relationship between energy transferred from the particle to the material per unit path length. The particle undergoes multiple scatters with the electromagnetic field of the orbital electrons of the material until all the energy of the proton has been fully deposited. For large particles such as protons, most of the energy is deposited at the end of its range, which is characterized by the Bragg peak. Dose for charged particles is mathematically described by the product of the LET and the distance traversed by the particle. FIG. 3 illustrates the difference in energy deposition for photons and protons. The dose from photons is distributed exponentially along the beam path, whereas protons will concentrate dose in tumor tissue while sparing proximal and distal tissue. This has important clinical implications because distal or proximal tissues may be dose limited organs. Protons deposit the majority of energy at the end of their range so that the dose to the tumor is maximized. Various treatment uncertainties force the use of additional margin around the tumor volume, which means additional normal tissue will be treated. Typical clinical practice is that a 3.5% margin is added to the target proximally and distally to compensate for proton range uncertainty. This typical margin is combined with margins for additional uncertainties and leads to a significant undesired dose to healthy tissue. This extra margin reduces the efficacy of proton radiotherapy, because the full advantage of the Bragg peak is not realized. These uncertainties prevent confirmation of where the Bragg peak will occur.

Computed Tomography Systems

Computed tomography is the axial, slice by slice digitization and discretization of three dimensional objects in which three dimensional image data sets are formed. The physical object is rendered into a three dimensional matrix of voxel values that are determined based on the radiometric characteristics of the object. CT images combine multiple 2D image projections taken at multiple discrete arc lengths around the object for a single slice.

A typical medical CT scanner is composed of (1) an X-ray source that is mounted to a gantry that allows the x-ray source to rotate 360 degrees around the patient; (2) a ring of multi row x-ray detectors that are used to measure the differential attenuation of the x-rays as they traverse the patient; and (3) a translational table that moves in and out of the CT gantry to allow a slice by slice measure of the x-ray attenuation.

Figure 17:
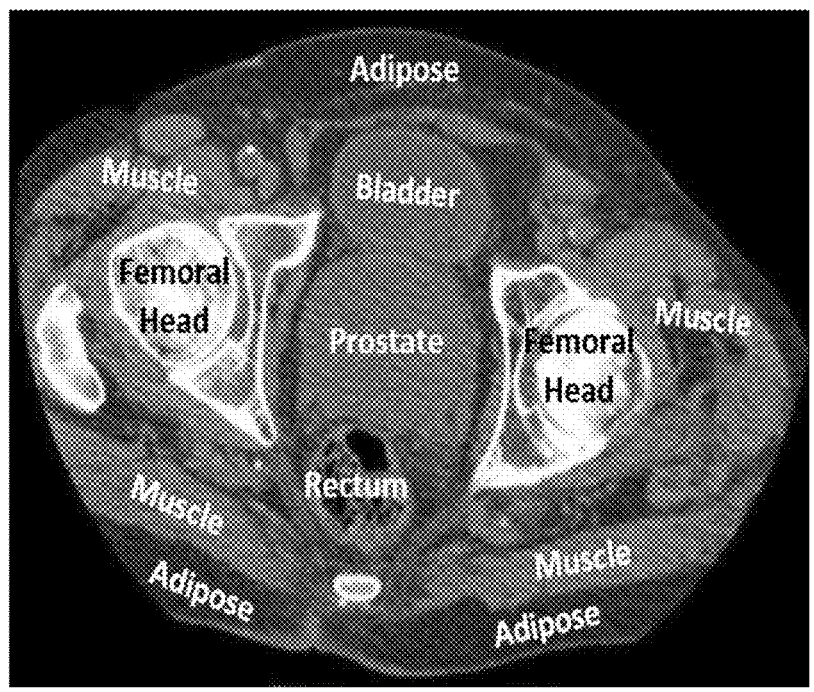
FIG. 17 is a CT image of a human male pelvis, with anatomical features labeled.
Figures 18, 19:
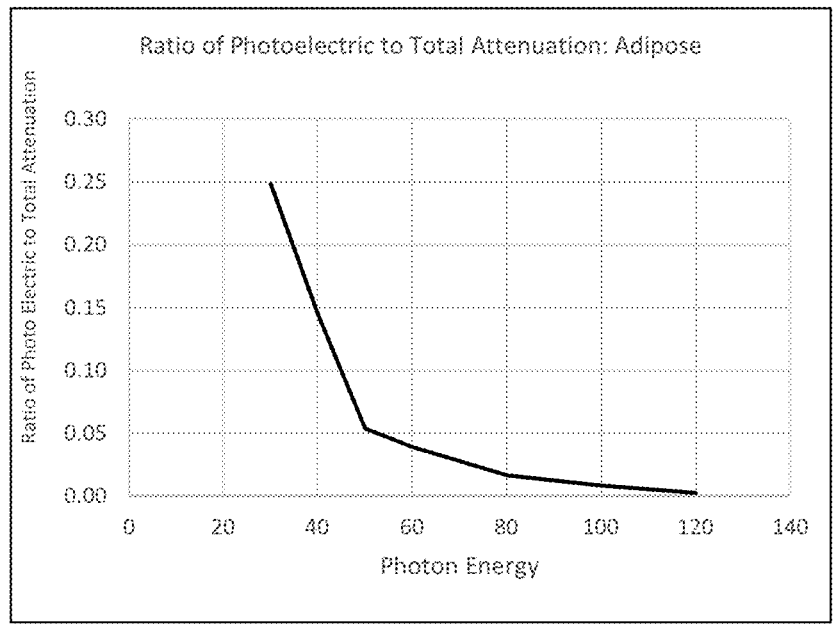
FIG. 18 is a graph showing the ratio of photoelectric effect to total attenuation for adipose tissue.
FIG. 19 is a table showing the ratio of photoelectric effect to total attenuation for adipose tissue at various energy ranges.
Figures 20, 21:
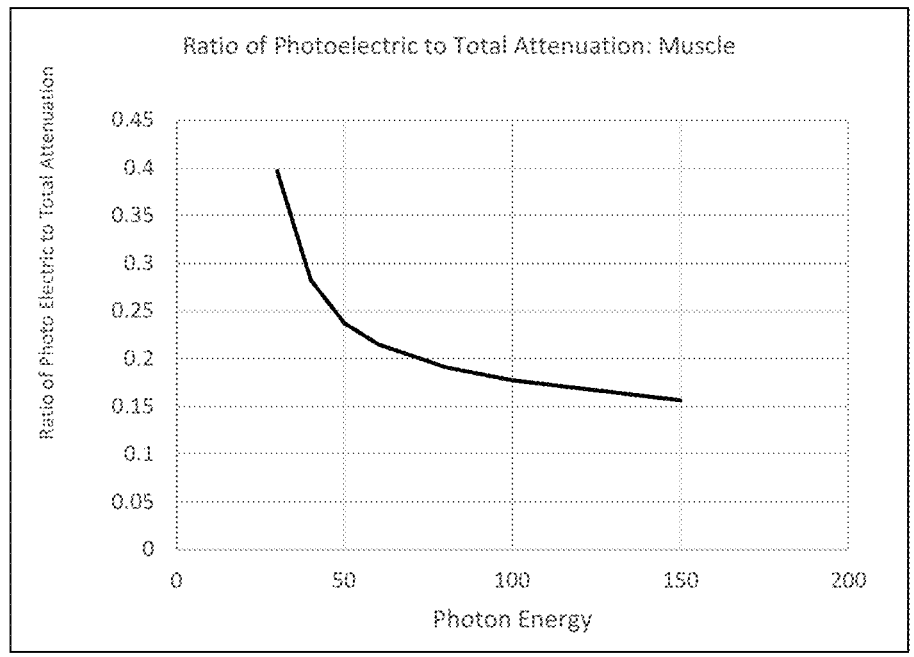
FIG. 20 is a graph showing the ratio of photoelectric effect to total attenuation for muscle tissue.
FIG. 21 is a table showing the ratio of photoelectric effect to total attenuation for muscle tissue at various energy ranges.
Figures 22, 23:
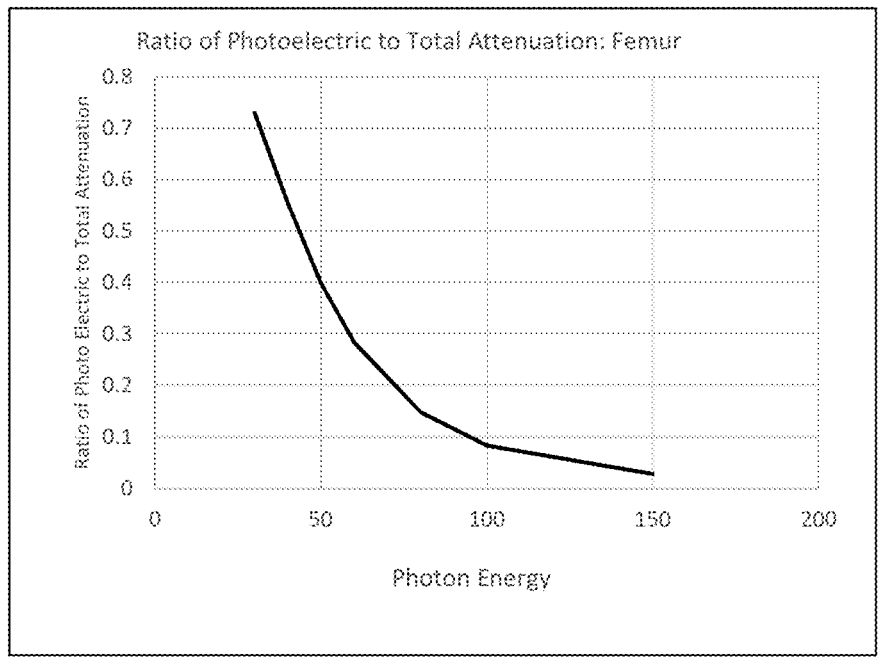
FIG. 22 is a graph showing the ratio of photoelectric effect to total attenuation for femur tissue.
FIG. 23 is a table showing the ratio of photoelectric effect to total attenuation for femur tissue at various energy ranges.
Figures 24, 25:
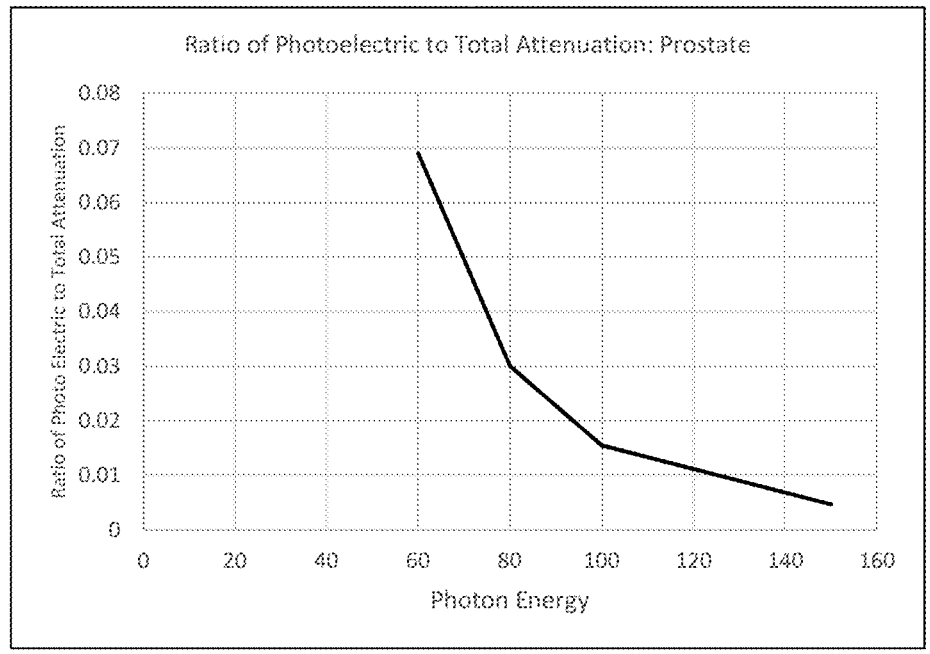
FIG. 24 is a graph showing the ratio of photoelectric effect to total attenuation for prostate tissue.
FIG. 25 is a table showing the ratio of photoelectric effect to total attenuation for prostate tissue at various energy ranges.

To create the x-ray radiation within the x-ray tube, electrons are accelerated and impact a tungsten target producing photon output that is poly energetic, in a process known as brehmsstralung (i.e., braking radiation or deceleration radiation). Typical acceleration potentials are between 100 and 140 kVp. Absorbers are used to shape the beam and remove lower energy photons that produce dose to the patient and do not contribute to the image. The radiation detectors comprise scintillation materials and are arranged in arrays of up to 900 detectors and vary by manufacture. The patient discretization in the x and y-axis are based on the number and size of detectors in a single row of the detector array. The z-axis patient discretization is based on the number of rows of detectors. FIG. 17 illustrates a single axial slice of a cylindrical object undergoing a tomographic imaging procedure. Once the single axial slice has been measured, the object will translate, and another slice will undergo a tomographic measurement.

The CT unit creates an axial image as a relative linear attenuation mapping of the patient geometry, utilizing equation 1 below.

$$I = I_o e^{\mu x} \qquad \text{Equation 1:}$$

I=attenuated output
$I_o$=initial output
µ=linear attenuated coefficient
x=depth in material To determine relative attenuation mapping, the output and detector response is measured. This is accomplished via air calibrations in which no attenuating materials are placed in the beam to determine the initial output. The value of I is determined by placing the patient in the beam path. This value is discretized based on the detector width and gives the one-dimensional radon transformation for a slice. Thus, the three-dimensional (3D) object has been transformed from a 3D space domain to a 1D radon domain.

This transformation shows the radiation intensity per unit length for an angle between the central axis of the object and the tube/detector orientation. Multiple radon transformations are measured for one axial slice. These radon transforms are then transformed into Fourier space, where a mathematical filter is applied to filter out high frequency noise that blurs the image. Once these filters have been applied, the image is back projected into Cartesian space with an inverse Fourier transformation, as normalized relative attenuation coefficients. Because the initial spectrum is measured during the air calibrations, Equation 1 can be used to determine the x-ray attenuation value, for each voxel of the human anatomy image. The normalized relative attenuation coefficient is expressed as a CT number and is back projected into the Cartesian space. A CT number is defined below in Equation 2.

$$CT \text{ Number} = \frac{\mu_x - \mu_{water}}{\mu_{water}} \times 1000 \qquad \text{Equation 2}$$

The poly energetic nature of the radiation beam makes the calculation of attenuation coefficients complex, since p is dependent upon energy, electron density, and Z. The total attenuation coefficient becomes a summation of the attenuation coefficients at a single energy. This complexity brings underlining uncertainty in the calculation of CT numbers. If the radiation spectrum in not well characterized then CT numbers will also have undesirable uncertainty. Table 1 lists exemplary CT numbers for selected human tissues.

TABLE 1

Common CT Numbers for Human Tissues

| Tissue | CT Number (HU) |
|---|---|
| Bone | +1000 |
| Liver | 40 to 60 |
| White Matter | −20 to −30 |
| Grey Matter | −37 to −45 |
| Blood | 40 |

TABLE 1-continued

Common CT Numbers for Human Tissues

| Tissue | CT Number (HU) |
| --- | --- |
| Muscle | 10 to 40 |
| Kidney | 30 |
| CSF | 15 |
| Water | 0 |
| Fat | −50 to −100 |
| Air | −1000 |

These values are utilized by the treatment planning system to calculate the dose to a patient. CT numbers must be converted into electron densities to correct for the heterogeneity of the patient. The correlation between the CT numbers and electron densities of different tissues is the prerequisite for accurate patient dose calculations in most modern radiotherapy treatment planning systems. For collapsed cone convolution (CCC) and analytical anisotropic algorithm (AAA) treatment planning systems, a pre-calculated energy deposition kernel is convolved with the radiation output from a linear accelerator to model the dose within the patient. CCC and AAA treatment planning systems utilize electron density as opposed to the linear attenuation coefficients to calculate dose deposition for photon radiation therapy. Monte Carlo based systems use a first principles methodology, which extracts the attenuation coefficient rather than the electron density. Typical treatment planning systems for proton radiation therapy use a convolution methodology which convolves the unperturbed proton beam with a beamlet in water.

This method compensates for inhomogeneity by multiplying the convolved proton beam with the fluence at a particular position. The fluence of the proton beam (if double scattered) consists of 1st and 2nd scatters, compensators, absorbers, modulators, and blocks. Each of these components contributes to the spectral flatness and symmetry of the beam. If the proton beam is a pencil beam, the fluence has contributions from divergences and beam size. These systems require knowledge of the stopping power relative to water to compensate for heterogeneity within the patient.

CT Number to Electron Density Calibration Curves

Electron density curves are created using electron density phantoms that have known compositions that replicate the radiometric characteristics found in human tissues, particularly electron density. Conventional phantoms are typically water equivalent cylinders with inserts of materials exhibiting a range of electron densities.

There are two typical methodologies of CT number to electron density (ED) curve measurements: (1) tissue substitute; and (2) stoichiometric.

Figure 4:
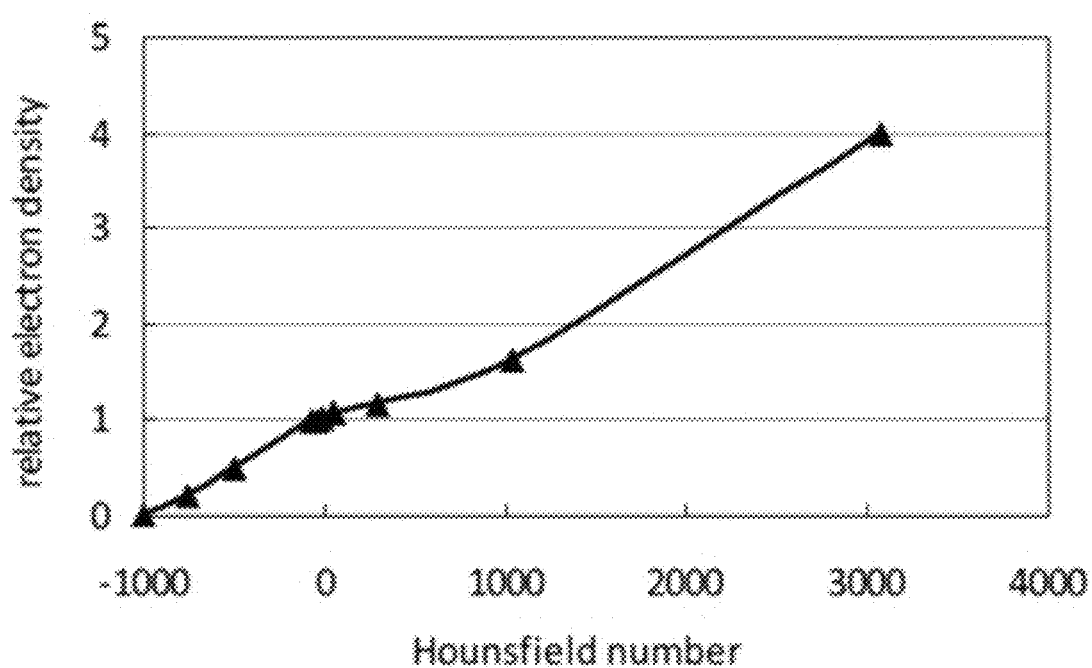
FIG. 4 is a graph showing an exemplary CT number to electron density calibration curve.

In the tissue substitute method, the CT to ED phantom is scanned and CT numbers are recorded for the known ED values from the ED inserts. A circular region of interest is placed on CT image showing the electron density insert and a CT number value is recorded for that insert. A CT number to electron density curve is formed by plotting the measured CT number to the known electron density value, as seen in FIG. 4.

The stoichiometric method enables calculation of theoretical CT numbers based on composition rather than measured values. The user parameterizes the radiation characteristics of the CT unit via measurement of a CT number to electron density calibration phantom. This is the preferred methodology for proton radiation therapy because of the higher level of certainty of the calibration compared to the tissue substitute method.

Error in the CT number to electron density calibration has direct proportionality to error in dose within proton radiotherapy. Due to the high distal gradient of the dose, this could lead to a 100% difference in dose to the target.

Existing Phantoms

Figure 5:
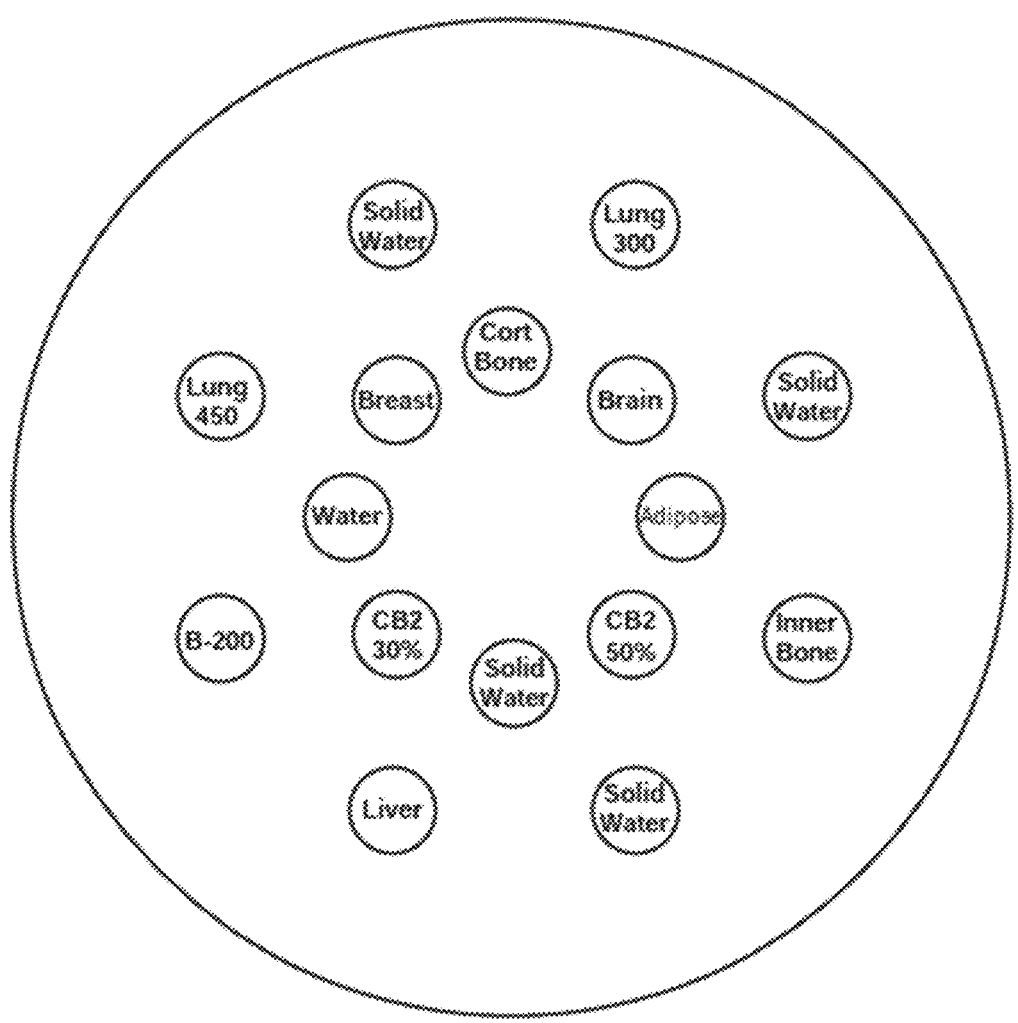
FIG. 5 is a depiction of a Gammex 467 Phantom (Gammex, Middletown Wis.).
Figure 7:
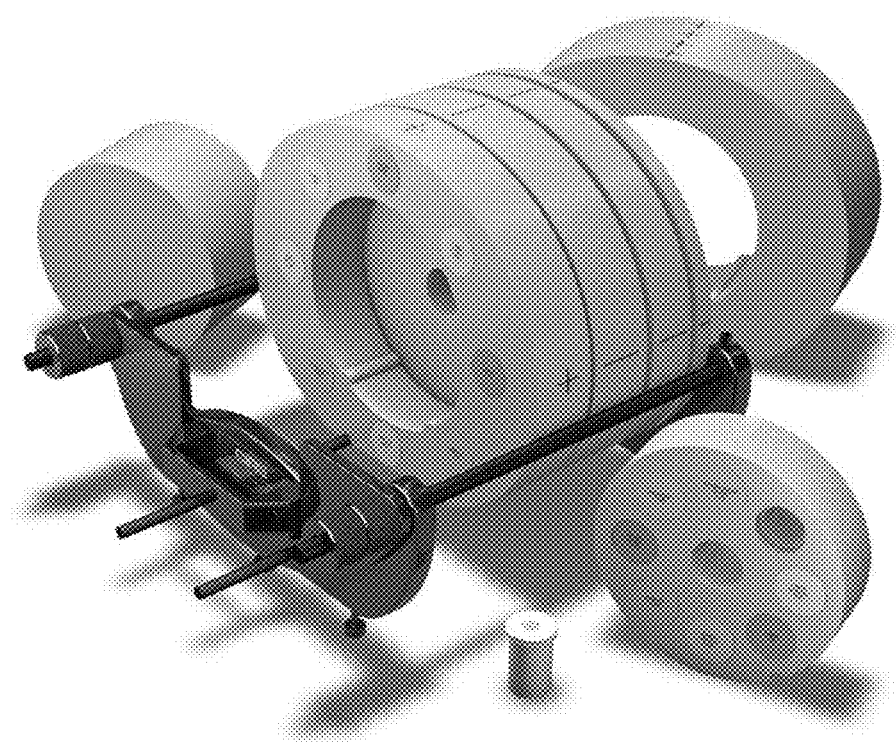
FIG. 7 is a depiction of a Model 062M Cone Beam Electron Density Phantom (CIRS, Norfolk, Va.).

The Gammex 467 model (FIG. 5) consists of a 33 cm diameter Solid Water® disk approximating the size of an average male pelvis. A matrix of sixteen 2.8 cm diameter holes in the disk hold interchangeable rods of various tissue and water substitutes The Model 062M (FIG. 7) consists of two nested disks made from Plastic Water®-LR, which can represent both head and abdomen configurations. Nine different tissue equivalent electron density plugs can be positioned at 17 locations within the scan field. Included is a water vial plug that can be filled with any fluid.

While these phantom models are well-characterized, they possess significant deficiencies in their ability to appropriately characterize CT numbers in different anatomical sites. Because of the radiation beam hardening due to attenuation in the phantom compared to the attenuation in the patient, the spectrum changes and thus the measured attenuation coefficients change. Beam hardening occurs when the lower energy photons are preferentially attenuated in a poly energetic beam. Beam hardening will occur relative to a material's radiometric properties. Materials with a higher electron density or Z will preferentially attenuate the lower energy photons relative to materials with low electron density or Z. Because of the difference in beam hardening, error is introduced in the measurement in CT numbers.

Water equivalent path length is the length of a material that is equivalent to the length in water that will attenuate an equivalent amount of radiation. Equation 3 shows how water equivalent path length relates to the length, the attenuation coefficient for an object, and the attenuation coefficient for water.

$$L_w = \int \mu_i dl / \mu_{water} \qquad \text{Equation 3:}$$

$L_w$=water equivalent path length
$\mu_i$=attenuation coefficient for object
$\mu_{water}$=attenuation coefficient for water
dl=length The average American male pelvis is 33 cm in diameter and reflects the physical size of the CT number to electron density calibration phantoms commercially available. The difference in water equivalent length at 81 keV between a standard phantom and human pelvis is illustrated herein. Based on the calculation for 81 keV photons, the water equivalent path length for the human pelvis is 1.45 times larger than that of the standard phantom. This means that there is 45% more attenuation of the radiation beam at 81 keV in the human anatomy as compared to the standard phantom. Thus, the measured CT number in the patient is different than the CT number for the same material in the phantom. This difference is greater at lower photon energies and with materials of higher Z because of the difference in photoelectric attenuation. For a pelvis that includes bone, the poly energetic beam will preferentially attenuate more low energy photons compared to the CT to electron density phantom. Because of the aforementioned preferential attenuation, the mean energy for the beam at the point of interaction is higher for the human pelvis as compared to the standard phantom.

The CT radiation beam is poly energetic; hence, varying attenuation is occurring for all energies from 30 keV to 120 keV that make up the beam. Water equivalence can be correlated with spectral variation, these variations lead to uncertainties in measured CT number. Inness, et al., *The dependence of computed tomography number to relative electron density conversion on phantom geometry and its impact on panned dose*, Australasian Physical & Engineering Sciences in Medicine 37: 385-91 (2014) confirmed that for CT number to electron density calibration curves, the phantom that is sampled must be comparable to the size of typical anatomy being clinical measured. If the scattering conditions of the calibration phantom do not mimic the scattering conditions in the patient, then the CT number that is measured for known electron densities could be proportionally uncertain. Further, error of CT number values can vary up to 3% based on the location of the material in the image. This lack of uniformity can once again be attributed to beam hardening across the CT spectra. Designing CT electron density phantoms that mimic patient anatomy, with materials that mimic patient radiometric qualities, which are size- and site-specific, will increase CT number certainty, thereby increasing patient dosimetry certainty.

Uncertainties in the electron density exist due to scatter and beam hardening of the CT radiation beam. Scatter and beam hardening affect the average energy of the beam, at the time of patient imaging relative to the time of calibration. Attenuation coefficients are energy dependent and the calculation of the CT numbers are sensitive to changes in the beam spectrum. If the beam spectrum that is used to measure electron density is not the beam spectrum utilized clinically, clinically significant errors in CT numbers can be expected. These errors have proportionality to spectral differences in beam at the time of calibration and at the time of clinical use.

Uncertainty Analysis

If the determination of CT numbers has uncertainty, the uncertainty in patient dosimetry will compare based on the treatment site. For photon radiation therapy, a 1% change in dosimetry is required for an 8% variation in electron density. This is not a crucial issue in photon radiation therapy dosimetry because photon interaction cross sections are relatively constant for the treatment energy range. On the other hand, proton dosimetry is proportional to electron density, such that a 1% error in electron density calibration leads to a 0.7% error in proton dosimetry. Error in the CT number acquisition adds error to the determination of patient radiometric values (electron density and stopping power), introducing uncertainty in patient dosimetry. Yang et al. report that the largest sources of error in the imaging chain for computed tomography is the beam hardening effect and patient scatter. Error is introduced by the parameterization formula used to calculate the theoretical CT numbers and tissue equivalence. These uncertainties in proton radiation dosimetry/range are listed in the tables of FIGS. 8 and 9, based on anatomical site. Each anatomical site has unique sources of uncertainty that contribute to an overall uncertainty estimate.

Tissue Equivalence

A tissue substitute material is selected to be radiometrically equivalent to the biological tissue type that is being modeled in a specific energy range. The radiation absorption and scatter for a thickness of tissue substitute material may match the radiation absorption and scatter for the thickness of biological tissue being mimicked. Typically, a comparison of attenuation coefficients and electron mass stopping powers meets the requirement to establish tissue equivalence for photon radiation. In embodiments, the bulk mass attenuation coefficient $$\left(\frac{\mu}{\rho}\right)$$

can be determined by summing the constituent mass attenuation coefficients $$\left(\frac{\mu}{\rho_i}\right)$$

for all the materials that comprises the tissue substitute. This can be mathematically described as follows:

$$\frac{\mu}{\rho} = \sum_i \omega_i \left(\frac{\mu}{\rho}\right)_i \qquad \text{Equation 4}$$

where oi is the relative weight of the ith chemical constituent. When a formulation is made, the ratio of the substitute material mass attenuation coefficient to biological tissue mass coefficient is calculated. The closer this ratio is to 1, the more closely the material mimics biological tissue. This methodology is termed as the "mixture rule."

$$\frac{\frac{\mu}{\rho_{Subs}}}{\frac{\mu}{\rho_{tissue}}} \qquad \text{Equation 5}$$

This same assessment is made for the stopping power $$\left(\frac{S}{\rho}\right)$$

of the material. Equation 6 (the mixture rule) indicates that the total mass stopping power is the constituent mass stopping power summed over the relative weight. The ratio of the substitute and biological tissue stopping power ratio (Equation 7) should be close to 1 for a material to be optimized as a tissue substitute.

$$\frac{S}{\rho} = \sum_i \omega_i \frac{S}{\rho_i} \qquad \text{Equation 6}$$

$$\frac{\frac{S}{\rho_{Subs}}}{\frac{S}{\rho_{tissue}}} \qquad \text{Equation 7}$$

The elemental composition of each tissue type is listed in Table 2 and considers only those elements that contribute 0.1% or greater to the organ mass. The radiation mass attenuation coefficient for each tissue type was determined using the XCOM computer code (National Institute of Standards and Technology, NIST) and the weighted elemental composition for the tissue. XCOM creates a discrete table of attenuation coefficients as a function of energy. In order to determine attenuation coefficients at clinically relevant energies, a least mean square regression of the log transformed attenuation coefficients from XCOM was performed with values from Table 2. Attenuation coefficients were determined for energies from 30 to 120 keV in 10 keV intervals.

TABLE 2

Elemental Composition of Prostate Tissues

| Tissue | H | C | N | O | Na | Mg | P | S | Cl | Ca | K | $P\left(\frac{kg}{m^3}\right)$ |
|---|---|---|---|---|---|---|---|---|---|---|---|---|
| Femoral Heads | 7.0 | 34.5 | 2.8 | 36.8 | 0.1 | 0.1 | 5.5 | 0.2 | 0.1 | 12.9 | | 1330 |
| Prostate | 6.4 | 12.1 | 2.2 | 78.7 | 0.1 | 0.02 | 0.1 | 0.1 | 0.2 | 0.01 | 0.2 | 1000 |
| Bladder | 10.6 | 11.5 | 2.2 | 75.1 | 0.1 | | 0.1 | 0.1 | 0.2 | | 0.1 | 1030 |
| Rectum | 6.3 | 12.1 | 2.2 | 78.8 | 0.1 | | 0.1 | 0.1 | 0.2 | | 0.2 | 1030 |
| Adipose #2 | 11.4 | 59.8 | 0.7 | 27.8 | 0.1 | | | 0.1 | 0.1 | | | 950 |
| Muscle | 10.2 | 14.3 | 3.4 | 71.0 | 0.1 | | 0.2 | 0.3 | 0.1 | | 0.4 | 1050 |

For photon attenuation and absorption processes (excluding pair production), near linear curves are produced when plotted on a log-log scale between 10-150 keV. Here, only regressions that had an $R^2$ of 0.9 and above were accepted for use. The linear regression provided an equation that allowed for the determination of attenuation coefficients at different clinically relevant energies that would be typical of a computed tomography spectrum.

$Z_{eff}$ Determination

For a chemical compound, the total attenuation coefficient per molecule is equal to the weighted sum (arithmetic mean) of the constituent molecule's cross sections.

$$\sigma_m = \Sigma n_i \sigma_i \qquad \text{Equation 8:}$$

Where $\sigma_m$ is the total cross section of a compound, $n_i$ is the number of atoms of the ith constituent of that compound, and $\sigma_i$ is the total cross section of the ith constituent element of that compound. The effective total cross section can be expressed as a function of per electron and per atom. This assumes that one can replace actual atoms of a given molecule with an equal number of identical (average) molecules.

$$\sigma_m = n\sigma_a = nZ_{eff}\sigma_e \qquad \text{Equation 9:}$$

$\sigma_a$ = Effective total cross section per atom
$\sigma_e$ = Effective total cross section per electron
$Z_{eff}$ = The effective Z for the compound
n = Total number of atoms in the molecule The generalized equation for effective Z for compounds is the ratio of the atomic cross section to the electronic cross section.

$$Z_{eff} = \frac{\sigma_a}{\sigma_e} \qquad \text{Equation 10}$$

$$Z_{eff} = \frac{\sum n_i \sigma_{ai}}{\sum n_j \frac{\sigma_{ei}}{Z_j}} = \frac{\sigma_a}{\sigma_e} \qquad \text{Equation 11}$$

A generalized equation for mixtures and compounds was developed by inserting the value $f_i$ which is the weighted fraction of the number of atoms per constituent element.

$$f_i = \frac{n_i}{\sum n_j} = \frac{n_i}{n} \qquad \text{Equation 12}$$

-continued $$Z_{eff} = \frac{\sum f_i \sigma_{ai}}{\sum f_j \frac{\sigma_{ei}}{Z_j}} \qquad \text{Equation 13}$$

Equation 13 was utilized to determine the $Z_{eff}$ for the tissues listed in Table 2.

Figure 11:
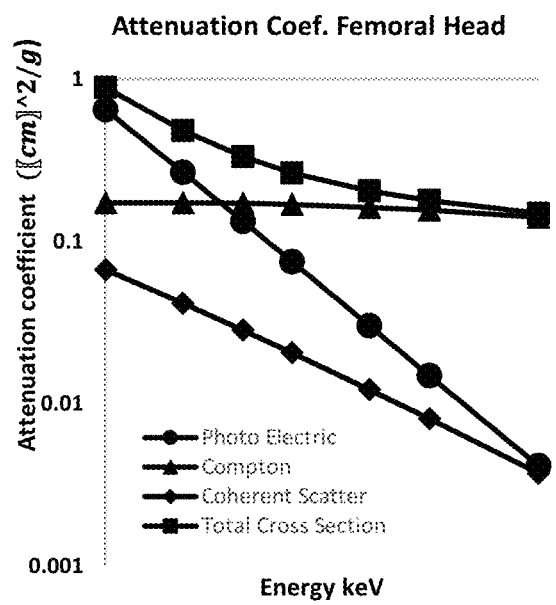
FIG. 11 is a graph showing the relationship between mass attenuation coefficient and the natural log of energy (keV) for femoral head tissue.
Figure 12:
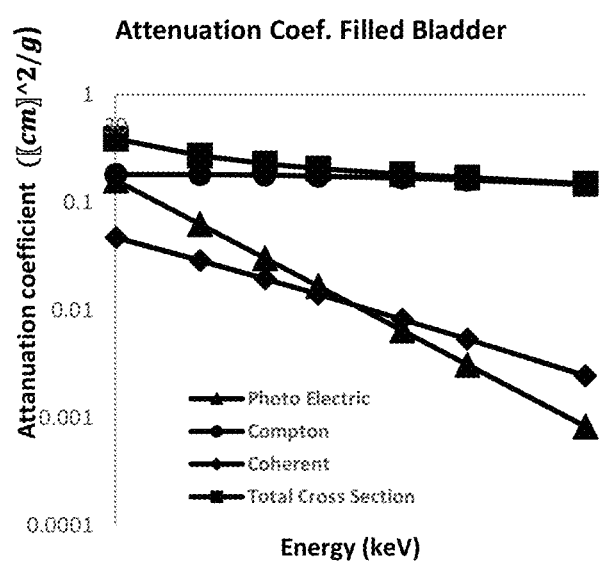
FIG. 12 is a graph showing the relationship between mass attenuation coefficient and the natural log of energy (keV) for filled bladder.
Figure 13:
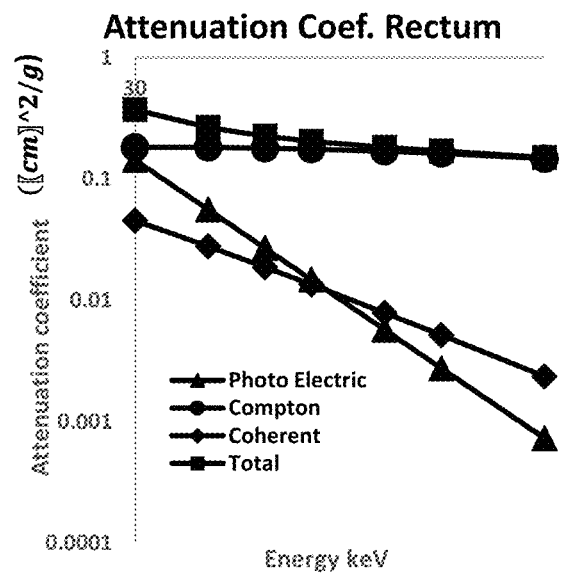
FIG. 13 is a graph showing the relationship between mass attenuation coefficient and the natural log of energy (keV) for rectum.
Figure 14:
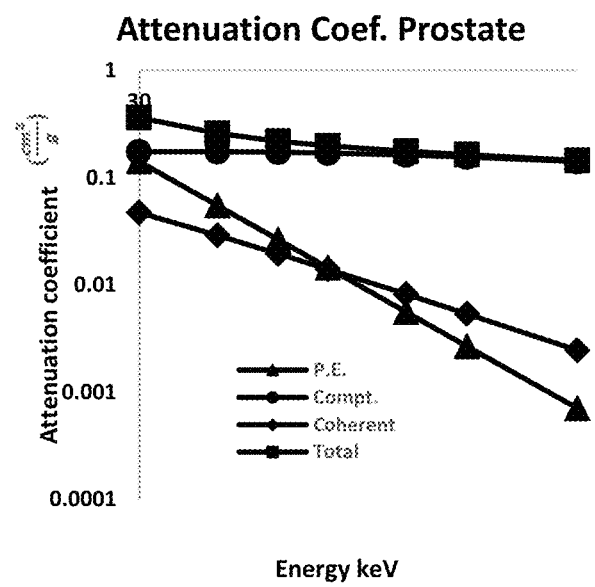
FIG. 14 is a graph showing the relationship between mass attenuation coefficient and the natural log of energy (keV) for prostate.
Figure 15:
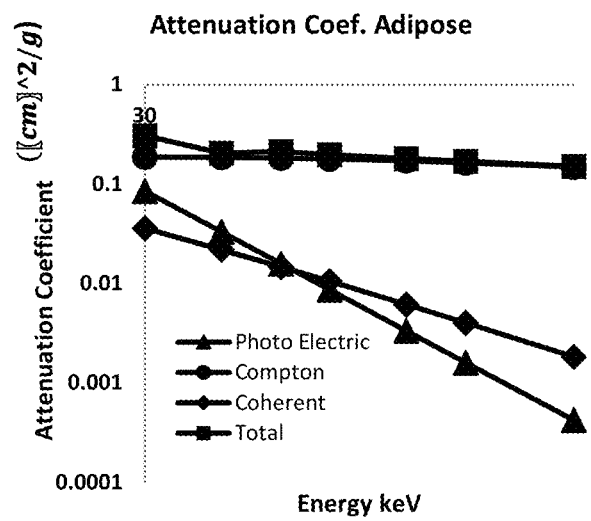
FIG. 15 is a graph showing the relationship between mass attenuation coefficient and the natural log of energy (keV) for adipose.
Figure 16:
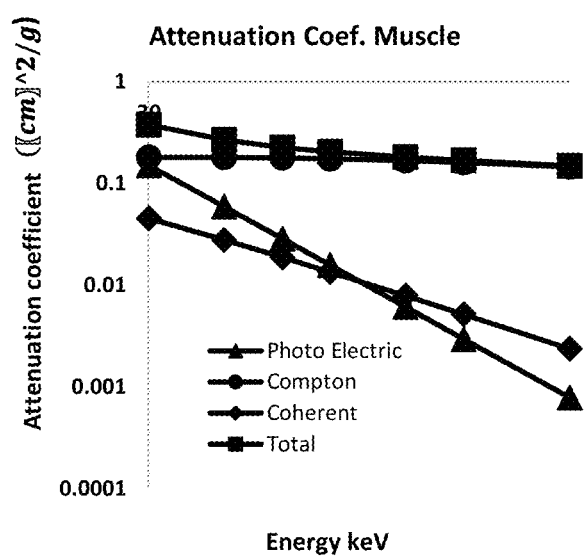
FIG. 16 is a graph showing the relationship between mass attenuation coefficient and the natural log of energy (keV) for muscle.

ICRU 44 and NCRP 23 Attenuation Coefficient Deconstruction & Tissue Substitute Design The constituent attenuation coefficients for ICRU 46/NCRP 23 tissues are visualized in FIGS. 11-16. The ordinate is the natural log of the mass attenuation coefficients, and the abscissa is the natural log of energy in keV. The data is displayed highlight the relative contributions of each interaction constituent for each tissue type. A sharp slope indicates an interaction constituent that falls off sharply with energy, which is typical of photoelectric effect and coherent scattering. The impact on the total attenuation coefficient will be based on the intercept of the constituent relative to the total cross section. This concept is illustrated in FIG. 11, which shows the attenuation coefficient constitution for femoral head tissue. At lower energies, the photo electric effect contributes in a significant manner to the total cross section. FIGS. 12-16 show the attenuation coefficient constituency for soft tissues of the pelvis, wherein the photoelectric effect has a significantly lower impact on the total attenuation coefficient, with a correspondingly smaller intercept. The Compton effect has a flat slope across all energy ranges for all tissues. The equation for these linearized attenuation coefficients will have some congruence with an ideal tissue substitute. The greater the difference between the Compton effect and the total attenuation coefficient, the larger the impact of photoelectric effect. This is significant because the difference between these two lines places a limit on the impact atomic number for the tissue substitute additive that will utilized, especially if spectral effects are taken into context. The greater the separation between the Compton effect and the total mass attenuation coefficient, the greater flexibility on the Z of the additive in the tissue substitute.

As expected, the component for photoelectric interactions is high for femoral head as compared to other tissue components. This is primarily due to the relatively high calcium and phosphorus constituents of bone as compared to the other biological tissues. The photoelectric effect has a larger significance at lower energies due to the dependence on $$\frac{1^3}{E}.$$

The relative impact of photoelectric interactions is low as compared to Compton interactions for all tissue types. Adipose tissue has a significantly lower contribution from photo electric effect as compared to other tissues that have higher Z elements as part of their composition. The homogeneity of the Compton mass attenuation data across all tissues is due to the dependence of Compton interactions on electron density. Electron density is approximately the same for all elements other than hydrogen, where the electron density is two times as high as compared to other elements. The tissues and tissue substitutes compare favorably. The photo electric attenuation coefficients for soft tissue are higher for the tissue substitutes as compared to the ICRU/NCRP tissue data. This is primarily due to the use of $CaCO_3$ as an additive, which has a higher Z as compared to the constituents of the ICRU/NCRP tissues. The impact of higher hydrogen content can be seen in the higher Compton attenuation coefficients for the ICRU/NCRP tissues. As can be seen from Table 2, the chemical composition of the biological tissues has a hydrogen composition range of 6.3% to 11.4% and the max difference between Compton mass attenuation values are 7.02%.

TABLE 3

| | $Z_{eff}$ (Tissue 44 and NCRP 23) | | | | | |
|---|---|---|---|---|---|---|
| | Energy keV | | | | | |
| Tissue | 30 | 40 | 50 | 60 | 90 | 100 |
| Femoral Head | 9.7 | 6.2 | 5.5 | 4.8 | | 4.3 |
| Prostate | 5.5 | 4.7 | 4.5 | 4.4 | | 4.3 |
| Bladder Filled | 4.7 | 3.8 | 3.6 | 3.5 | | 3.4 |
| Adipose | 3.8 | 3.3 | 3.2 | 3.1 | | 3.0 |
| Muscle | 4.7 | 3.8 | 3.7 | 3.5 | | 3.4 |
| Rectum | 4.6 | 3.7 | 3.6 | 3.5 | | 3.4 |

Table 3 shows the effective Z for the tissues of the pelvis designed for an energy of 81 keV. The effective Z drops off precipitously between 30 keV and 60 keV for all tissues except for adipose. The higher the constituent components Z the more precipitous the fall off between 30 to 60 keV because of the impact of photo electric at these energies. Adipose tissue is relatively stable from 50 keV to 120 keV because of its low Z constitution, which makes the most likely interaction across this energy range Compton.

Determination of Constituent Component Weightings for Substitute Materials

Substitute materials were designed as multi-component formulation, comprised of a base material and multiple additive materials. A base material is a material that will typically have the larger volumetric contribution to the substitute material formulation. A suitable base material allows for malleability and casting, while having low enough attenuation properties that simulation of soft tissue or bone tissue can be accomplished by adding an additive material with higher attenuation properties. Attenuation is a function of both chemical composition and density. Hence, both the attenuation properties and the density of the base material are selected to be similar to that of the biological tissue. Typically, additives have a Z of less than 20 because of the difficulty of matching the attenuation properties for energies between 10 and 100 keV. If the Z of the additive material is too low, the capacity of the base material may be overwhelmed. Hence, the selection of an additive material is made in view of both attenuation properties and volume efficiency.

In embodiments, polyurethane ($C_{27}H_{36}N_2O_{10}$) is a suitable base material for tissue substitute materials. For the purposes of this disclosure, the aforementioned exemplary chemical equation is employed. Polyurethane is easy to mold and can be utilized with an additive to simulate a wide variety of tissue types. To determine the attenuation properties of polyurethane, XCOM was utilized to produce a tabular mass attenuation coefficient vs. energy data set. Linear log-log linear regression was utilized for each attenuation coefficient for an energy of 81 keV. Multiple additive materials were considered and $CaCO_3$, Teflon, and LiOH were selected due to their ease of use and ubiquity in the field.

The attenuation coefficient was determined by regression analysis with the desired clinically relevant energy as the variable input (81 keV). For this method of attenuation deconvolution, the biological tissue's attenuation coefficient is designed around a specific energy and a specific interaction type (Photoelectric, Compton, Pair Production, Total). $C_{femoral\ head\ @\ 81\ keV}$ is the attenuation coefficient for the femoral head at 81 keV. These attenuation values for a specific mean energy and anatomical site were determined for all interaction processes and for all the tissue types (Table 1).

Equations have been developed to determine the appropriate constituent material ratio (D. R. White). Additives can be selected efficiently and correctly by correlating the linearized attenuation coefficient values of the biological tissue, the tissue substitute base material, and the tissue substitute additive material. With the constituent photon, interactions were tabulated using equation 14, 15, and 16 to determine the appropriate weightings for components A and B.

$$C_x(E)=C_S(E) \qquad \text{Equation 14:}$$

$C_x$=Biological Tissue Attenuation Coefficient
$C_S$=Tissue Substitute Attenuation Coefficient $$C_S(E)=\omega_a C_a(E)+\omega_b C_b(E) \qquad \text{Equation 15:}$$

$C_a$ (E)=Tissue Substitute Additive Attenuation Coefficient
$C_b$ (E)=Tissue Substitute Base Attenuation Coefficient
$\omega_a$, $\omega_b$=Weighting Factor For the Additive and Base Material $$\omega_a+\omega_b=1 \qquad \text{Equation 16:}$$

White's method in conjunction with mathematical optimization were utilized to determine the appropriate weightings of each constituent material.

White's method linearizes the mathematical operation for tissue equivalent material design. Linear is defined as not raising any of the variables to powers and not transforming the variable with transcendent functions (example: sin and cos). In linear programming this is known as Standard Form. Simplex optimization method requires: (1) objective function must be linear; (2) all constraints must be linear; and (3) all variables are non-negative.

| Objective Function | $\Sigma\mu(E)_{Total\ X} - \Sigma\mu(E)_{Total\ S}$ |
|---|---|
| Constrain 1 | $\dfrac{\sum \mu(E)_s}{\sum \mu(E)_x} = \leq$ Normalized Relative Error |
| Constraint 2 | $\Sigma\omega_i = 1$ |

The objective function minimizes the difference between the total attenuation coefficient for biological tissue and the tissue substitute while constraint 1 ensures the variance at energy ranges is limited. Constraint 2 ensures that the sum of the relative weightings of each component is equal to 1.

Error Propagation Analysis of Tissue Equivalent Material

Uncertainties in measured electron density exist due to scatter and beam hardening of the CT radiation beam as it traverses the object. Attenuation coefficients are energy dependent, thus the calculation of the CT numbers are sensitive to changes in the photon energy spectrum. If the photon energy spectrum used to measure electron density for calibration is not the photon energy spectrum utilized clinically, significant errors in electron density measurements can be expected. These errors have proportionality to spectral differences in the beam at the time of calibration and at the time of clinical use. If the scattering conditions of the calibration phantom do not mimic the scattering conditions in the patient, then the CT number that is measured for known electron densities may be proportionally uncertain. For CT to HU calibration curves, the phantom that is sampled should be comparable to the size of typical anatomy being clinical measured. Error of CT number values can vary up to 3% based on the location of the material in the image. This reflects a lack of uniformity that can be attributed to beam hardening across the CT spectra. By designing CT electron density phantoms that mimic patient anatomy, with materials that mimic patient radiometric qualities and are size- and site-specific, CT number certainty can be increased, thereby increasing patient dosimetry certainty.

If the determination of CT numbers has uncertainty, the uncertainty in patient dosimetry will compare based on the modality and treatment site. For photon radiation therapy, a 1% change in dosimetry requires an 8% variation in electron density. This is less relevant in photon radiation therapy dosimetry, primarily because photon interaction cross sections are relatively flat for the treatment energy range. Protons, on the other hand, have a closer proportionality to electron density. Errors occur in the treatment planning process because CT technology and reconstruction has not effectively dealt with the issue of patient scatter and beam hardening that occurs as a result of CT acquisition. This adds error to the CT numbers that are acquired by the system and adds error to the determination of patient radiometric values (electron density and stopping power), thus introducing uncertainty in patient dosimetry. The largest sources of error in the imaging chain for computed tomography is the beam hardening effect and patient scatter and the parameterization formula used to calculate the theoretical CT numbers and tissue equivalence. Yang, et al. discloses the uncertainty in proton radiation dosimetry/range based on anatomical site, as shown in the tables set forth in FIGS. 8 and 9.

For each anatomical site, different uncertainty sources have different magnitudes of contributions to the overall uncertainty. The primary contributors to proton radiation therapy dose/range uncertainty are due to CT imaging and CT to electron density phantom tissue equivalency. By reducing uncertainty in these areas, a significant uncertainty in these treatments can be reduced.

Tissue equivalent material formulation seeks to minimize the variance between anatomic tissue and tissue substitute radiometric characteristics. Although this is a straightforward concept, in practice this can be a challenge to achieve, because of the stoichiometric differences in tissue substitutes and anatomic tissue. Minimizing variance is further complicated by the use of polychromatic photon radiation beams, which require knowledge of photon attenuation coefficients for discrete energies in the energy range of interest.

A further complication in the clinical CT setting arises due to patient anatomy-specific beam hardening. Beam hardening creates variance between the spectra of the photon radiation beam that exits the CT (known spectra) and the spectra of the photon beam that interacts with the tissue. The difference in spectra induces an error in the determination of the effective mass attenuation coefficient. By understanding how systematic errors are introduced, due to the variance between tissue substitutes and anatomic tissues and the modulation of the CT spectra in different anatomical environments, design emphasis can be placed on the energy ranges and components that will have the greatest impact on overall variance in clinical environments. This changes the paradigm from developing tissue equivalent materials solely based on tissue substitute to anatomic tissue discrepancy, to also considering the surrounding scattering environment. In a prostate model, this considers all the tissues that are a part of the prostate tissue system, which includes adipose, bone, muscle, bladder, and rectum as secondary scatters.

In embodiments, tissue equivalent material is formulated for a single photon energy. Attenuation coefficients for specific photon interactions, i.e., photoelectric, coherent scatter, and non-coherent scatter, have discrete values based on a single energy. This is mathematically described as follows.

$$\mu(E)_{Total} = \int_{Min\ Energy}^{Max\ Energy} \mu(E)_{Photo\ Electric} + \int_{Min\ Energy}^{Max\ Energy} \mu(E)_{Coherent\ Scatter} + \int_{Min\ Energy}^{Max\ Energy} \mu(E)_{Incoherent\ Scatter}$$

Equation 17:

While this mathematical formulation is appropriate for radioactive materials that have discrete energies, it fails to completely describe the attenuation characteristics of a material for a poly energetic photon beam. To formulate tissue equivalent material for a poly energetic beam, material radiometric properties must be considered for the entire photon energy spectrum of interest. Because discrete attenuation coefficients describe only a small portion of the total photon radiometric characteristics, the Effective Attenuation Coefficient must be utilized. The effective attenuation coefficient is the summation of the discrete attenuation coefficients for the entire energy range of interest. The effective attenuation coefficient is mathematically described as:

$$\mu(E)_{Total} = \int_{Min\ Energy}^{Max\ Energy} \mu(E)_{Photo\ Electric} + \int_{Min\ Energy}^{Max\ Energy} \mu(E)_{Coherent\ Scatter} + \int_{Min\ Energy}^{Max\ Energy} \mu(E)_{Incoherent\ Scatter}$$

Equation 18

Equation 18 describes the attenuation coefficient for a continuum. While mathematically elegant, this is a challenge to implement in practice. Manufacturing materials with an effective attenuation coefficient requires a well characterized photon spectra, knowledge of anatomical tissue material radiometric and physical characteristics, knowledge of tissue equivalent material component radiometric and physical characteristics, and complex mathematical optimization.

To determine the total error associated with the tissue equivalent material, an analysis of the spectral characteristics for which the tissue will be designed is carried out. Because the polychromatic continuum does not produce the same number of photons for all energies, the error associated with the measurement of tissue equivalent material compared to anatomical tissue is significantly impacted by the relative number of photons produced at different energies. For example, photons produced between 30 to 40 keV for the CT spectrum only represent 6% of the total photon fluence, while photons produced between 60 and 70 keV represent approximately 20% of the photons produced for a CT continuum. This means that the errors in tissue equivalent material attenuation coefficients for the energy range between 30 and 40 keV propagate for 6% of the total interactions. While for errors in attenuation coefficients between 60 and 70 keV propagate through 20% of the total interactions for the CT spectra. This analysis can be applied because CT detection systems are not spectral detectors but integrated detectors, meaning they do not measure discrete photon energy fluence but the total number of photons that reach the surface of the detector. This allows for an approach to tissue substitute material design that takes into context the conditions that it will be measured under clinical conditions. In embodiments, the importance of energy ranges are weighted based on the probability of the photon being produced in the spectrum and the probability of that photon interacting with the tissue of interest. The geometry and scattering environment will impact whether or not a photon will interact with the tissue of interest, and therein its contribution to propagated error. Attenuation coefficients for photon energies that have a higher importance will be match with a higher degree of accuracy as compared to photons that do not. In embodiments, the expected error is less than 3% for attenuation coefficients for all energy ranges.

With integrated detection systems, the propagated error is influenced by the fact that photons in the lower energy region may not reach the detector because of the higher probability of interaction in surrounding tissues, and thus will not contribute to the integrated signal in both the tissue equivalent material setting (when an anatomically accurate phantom is utilized) and the anatomical tissue setting. This concept gives distinction to primary and secondary attenuation, which involves viewing tissue substitute design for not only the tissue in question but also the surrounding anatomical tissues that the photon will interact with prior to reaching the tissue in question. Primary scattering occurs in the tissue of interest, for example if diagnosis in the prostate is the clinical end point, the prostate is the primary scatterer. Secondary scatter comes from adipose, muscle, and femoral bone that is along the path of the radiation beam prior to interaction with the prostate or other tissues of interest. Secondary scatter hardens the radiation beam, changing the spectral characteristics prior to interacting with the prostate. Relative secondary attenuation can lead to either a harder or softer photon energy fluence when comparing phantom conditions and anatomical conditions. The relative beam hardening condition is influenced by both the relative size and the relative stoichiometric composition and will impact the propagated error.

For clinical prostate imaging, the photon fluence that reaches the prostate is significantly harder relative to the fluence that exits the CT unit because the position of the femoral heads relative to the prostate, other anatomical secondary scatters and the prostates medial position anatomically. FIG. 17 is an exemplary clinical image, with different tissues labeled.

For the prostate, tissue substitute design accuracy is most significant at the mid to high range of the CT photon spectrum. For adipose tissue, which is anatomically placed at the periphery, a higher degree of accuracy is required for the entire photon energy range. This is because adipose tissue is exposed to the entire photon spectrum of the CT scanner. Appropriately accounting for the level of precision and accuracy required for tissue substitute design, allows for optimized use of resources in formulating tissues and manufacturing tissue substitutes. The return on calculational investment for ensuring that the prostate tissue equivalent material matches precisely for lower energies is relatively low, while for fat the return on investment is significant.

When tissue equivalent materials do not appropriately match the radiometric and physical characteristics of anatomical tissues, a systematic error is introduced. The total error based on variance in effective Z and electron density can be described by the following equation:

$$\sigma(E, T) = \sum_{E_0}^{E_F}(\sigma(T, E)_{Photoelectric}) + (\sigma(T, E)_{Compton}) \qquad \text{Equation 19}$$

$\sigma(E, T)$ = Total Variance in effective attenuation coefficient $\sigma(T)_{Z_{effective}}$ = Variation in effective Z between anatomic tissue and tissue subs $\sigma(T)_{Electron\ Density}$ = Variation in electron density between anatomic tissue and tissue subs $w(E, T)_{photoelectric}$ = Weighting Factor for error due to variation in photoelectric effect $w(E, T)_{compton}$ = Weighting Factor for error due to variation in compton effect The error is separated into two parts based on the variation in effective Z and electron density. This variation is both dependent on tissue type and energy.

The individual error for effective Z and electron density are mathematically treated below:

$$du = \left(\frac{\partial u}{\partial x}\right)_{y,z} dx + \left(\frac{\partial u}{\partial y}\right)_{x,z} dy + \left(\frac{\partial u}{\partial z}\right)_{y,x} dz \qquad \text{Equation 20}$$

where u is the propagated error of the measured effective attenuation coefficient or electron density as a function of tissue type. The variables x, y, and z represent attenuation values of fat, femoral heads, and prostate respectively. dx, dy, and dz are the variation between the attenuation coefficients of the tissue equivalent material and the anatomical tissue. This formula may be further modified to take into account the relative magnitude of photon energy that interacts with the tissue.

$$du = \int_{E_O}^{E_f}\left(\frac{\partial u}{\partial x(E)}\right)_{y,z} dx + \int_{E_O}^{E_f}\left(\frac{\partial u}{\partial y(E)}\right)_{x,z} dy + \int_{E_O}^{E_f}\left(\frac{\partial u}{\partial z(E)}\right)_{y,x} dz \qquad \text{Equation 21}$$

This modification propagates the error over the entire energy spectrum for each tissue type.

The relative magnitude of the energy fluence contributes to the overall error as well. To factor this into the error assessment, a weighting factor will is applied to the error based on the relative contribution of the photon energy the error is being propagated for. This is done mathematically by the following equation:

$$w_i = \frac{N(E)}{\sum_{E_o}^{E_F} N(E)} \qquad \text{Equation 22}$$

This equation can be applied iteratively to modify the error propagation equation to account of the relative contribution of error as a function of photon energy fluence. This is done mathematically by the following equation:

$$du = \int_{E_o}^{E_f} \left(\frac{\partial u}{\partial x(E) w_i}\right)_{y,z} dx + \int_{E_o}^{E_f} \left(\frac{\partial u}{\partial y(E) w_i}\right)_{x,z} dy + \int_{E_o}^{E_f} \left(\frac{\partial u}{\partial z(E) w_i}\right)_{y,x} dz \qquad \text{Equation 23}$$

This treatment of error analysis creates a mechanism to scrutinize which energy regions are the most important to match in a clinical CT phantom and underscores the importance of matching the scatter environment for phantoms that are utilized in a poly energetic environment. By analyzing the error, an informed decision can be made as to which energy regions impact the error for tissue systems. The goal in analyzing error with this method is to match tissue component contributions that minimize the overall error while potentially increasing the error at discrete energies. This saves resources and focuses tissue substitute design on the components that impact the overall error with a larger magnitude.

Error Analysis for Prostate Tissue Imaging
Anatomic Tissue Radiometric Characteristic Analysis:

For poly energetic photon radiation beams an analysis of the interactions as a function of energy needs to be conducted for the relevant tissues. Attenuation coefficients from ICRU Report 44 were plotted and a linear regression was performed to determine the ratio of the photoelectric effect to the total attenuation component. This analysis gives an indication as to the systematic error that could be introduced based on a mismatch of effective atomic number. Higher contributions of photo electric interactions create a higher error if effective Z isn't appropriately matched between anatomic tissues and tissue substitutes. Results are shown in FIGS. 18-25.

This impact is not ubiquitous for all interactions, but dependent on the energy of the photons under consideration. The impact of photo electric is most significant for low energy photons and high effective Z materials. The ratio of photoelectric to total photon interactions gives a weighting factor for the error for the energy range of interest. For example, in regions where the photoelectric effect accounts for 15% of the interactions a mismatch in the effective Z would only account for 15% of the total error in the effective attenuation coefficient.

CT Spectrum Propagated Error Analysis

Figures 26, 27:
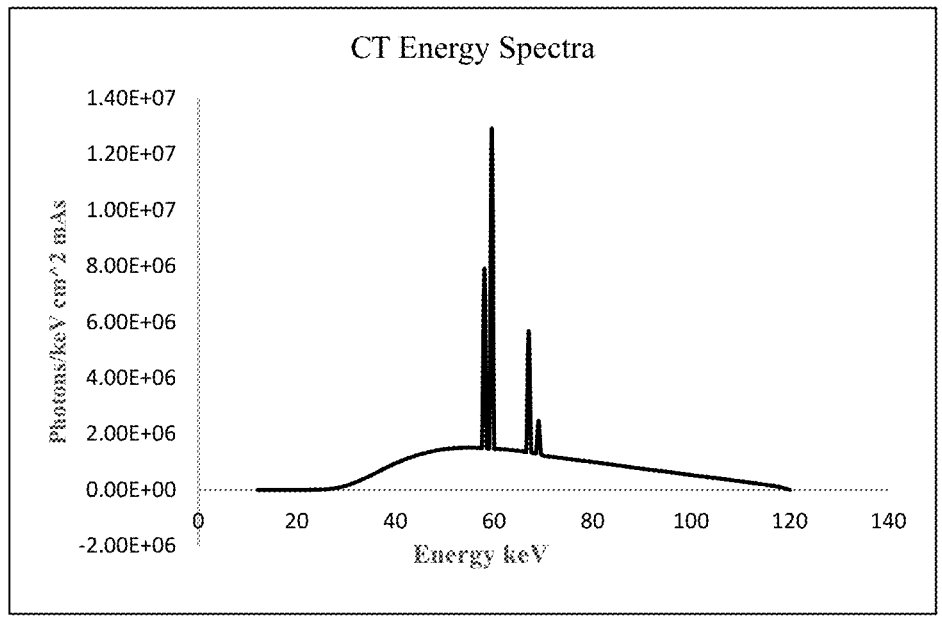
FIG. 26 is a graph showing CT energy spectra modeled with SpekCalc® software.
FIG. 27 is a table showing the relative contributions of each energy range to the CT energy spectra of FIG. 26.

The CT spectrum was modeled with the SpekCalc software. The photon energy spectrum is displayed in FIGS. 26-27. As shown in FIGS. 26-27, the relative contributions at the extremes of the spectrum is low. At the higher extreme, the primary requirement for radiometric equivalence is primarily a function of incoherent scatter and accounts for 2.04% of the total photon fluence. This requires a matching the electron density with a high degree of accuracy. At the lower extreme, radiometric equivalence will be based on the photoelectric effect and accounts for 5.64% of the total interactions. Matching the effective Z in the tissue substitute material is the primary endpoint in this energy range. The energy regions between the extremes are dominated primarily by incoherent scatter.

Tissue Harden Beam Characterization New Phantom

Figure 28:
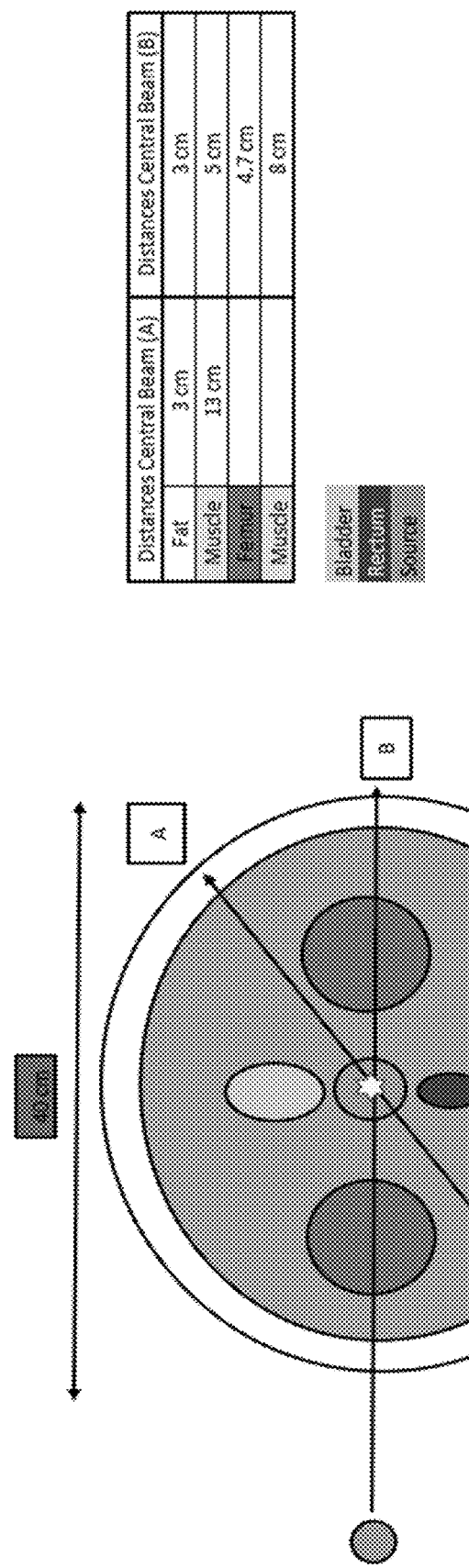
FIG. 28 illustrates Path A and Path B beams passing through an exemplary phantom according to one or more embodiments of the present disclosure.
Figures 29, 30:
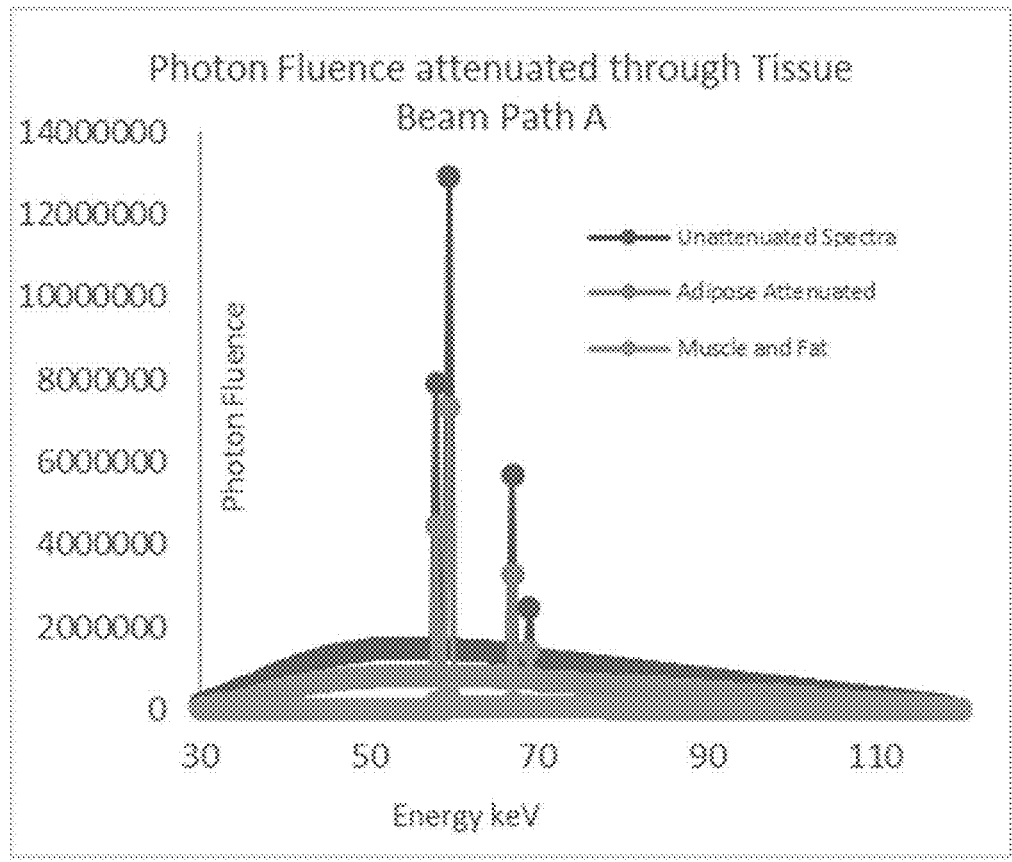
FIG. 29 is a graph showing photon fluence attenuated through tissue beam path A of FIG. 28.
FIG. 30 is a table showing average energy of selected tissue attenuators.
Figures 31, 32:
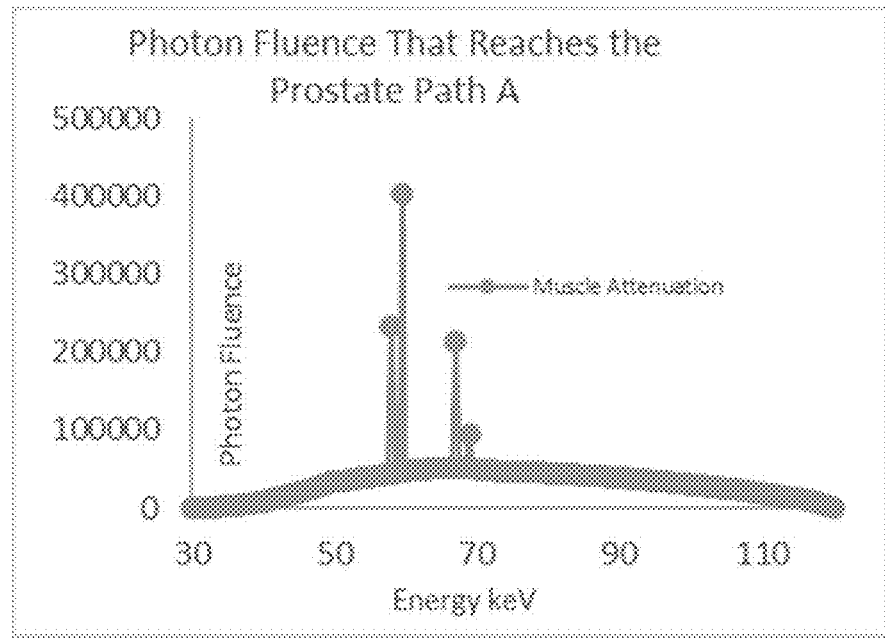
FIG. 31 is a graph showing photon fluence that reaches the prostate via Path A of FIG. 28.
FIG. 32 is a table showing relative contribution of different energy ranges (keV) to the total spectrum at the prostate for Path A of FIG. 28.

To assess how beam hardening impacts the measurement of the effective attenuation coefficient, finite element analysis was utilized. An anthropomorphic phantom with ICRU equivalent tissue material was designed. The calculated CT spectrum was attenuated through each tissue section and the resultant spectrum was determined based on the paths at the extremes of attenuation (FIG. 28). Path A is posterior oblique beam that only passes through adipose and muscle and is the lowest path of attenuation prior to interacting with the prostate (center). Path B passes through adipose, muscle, and femur prior to interacting with the prostate.

The geometry of the phantom was designed based on retrospective data obtained through an IRB approved study. Average dimensions of the distance from femur centroids, position of the bladder and rectum relative to the femur centroids, and the parenchyma girth were design parameters. A 3 cm adipose ring was utilized in the phantom assessment, although different dimensions may also be used.

Referring to FIGS. 29-32, the primary attenuator in geometry A is 13 cm of muscle tissue. The average energy of the poly energetic photon beam that reaches the prostate is 74.2 keV. This is an increase of 7.9 keV for the average energy attenuated by geometry A, as compared to the unattenuated photon spectra.

The primary energy bins that were preferentially attenuated were in the energy ranges between 30 and 60 keV for path A. The relative fluence begins to increase in the energy range between 60 and 70 keV.

Figures 33, 34:
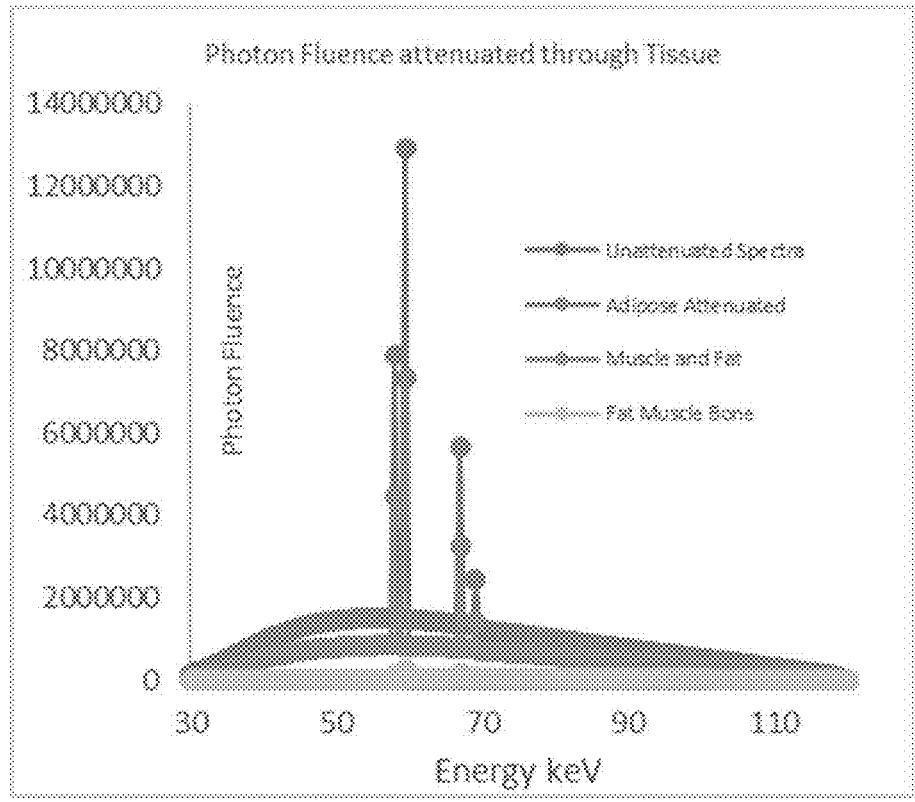
FIG. 33 is a graph showing photon fluence attenuated through selected tissues.
FIG. 34 is a table showing average energy (keV) of selected tissue attenuators.

The resultant attenuated spectra from beam B are visualized in FIGS. 33-34. As can be seen from the table of FIG. 34, the average energy increases 15.5 keV over all the tissues that are traversed. The beam becomes significantly harder due to the high Z femoral head that is along the beam path.

Figures 35, 36:
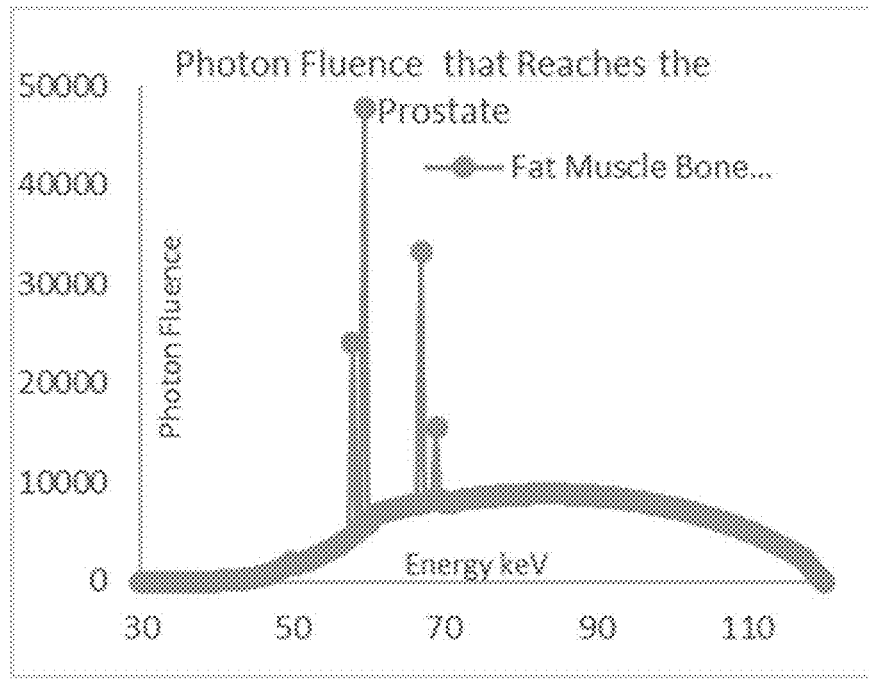
FIG. 35 is a graph showing photon fluence that reaches the prostate via Path B of FIG. 28, according to one or more embodiments of the disclosure.
FIG. 36 is a table showing relative contribution of different energy ranges (keV) to the total spectrum for the prostate for Path B of FIG. 28.

As can be seen in FIGS. 35-36, the energy bins at the lower end of the spectra have less than 1% of the cumulative fluence. For the energy bin between 50 and 60 keV the relative fluence decreased by 50%. The energy bins between 80 to 120 increased their relative contributions to the overall spectrum by at least 100%.

Impact of Adipose Thickness on Error

Adipose was modeled with the same principles as Path A and Path B of the anthropomorphic phantom. The unattenuated photon spectrum was attenuated through 3 cm, 6 cm, 9 cm and 12 cm of ICRU 44 Adipose #3 tissue, results for which are shown in FIGS. 37-38. As shown in FIG. 39, the normalized spectrum shows that the photon fluence maintains the same relative energy values from the 3 cm to 12 cm thickness.

The photon beam does not harden significantly with varying thicknesses of adipose as can be seen from the average energy remaining nearly constant from 3 cm to 12 cm and from the congruence of the normalized energy fluence curves. This suggest that for 120 kVp poly energetic CT photon spectra, the introduction of fat doesn't harden the spectra, but scales it. Although, the reduction of the radiation spectra due to fat attenuation could induce streaking artifacts due to photon starvation at the detector. In embodiments, streak artifact induction may also be accounted for in the analysis of error.

Beam Hardening Characterization for Commercially Available Phantoms

Figure 40:
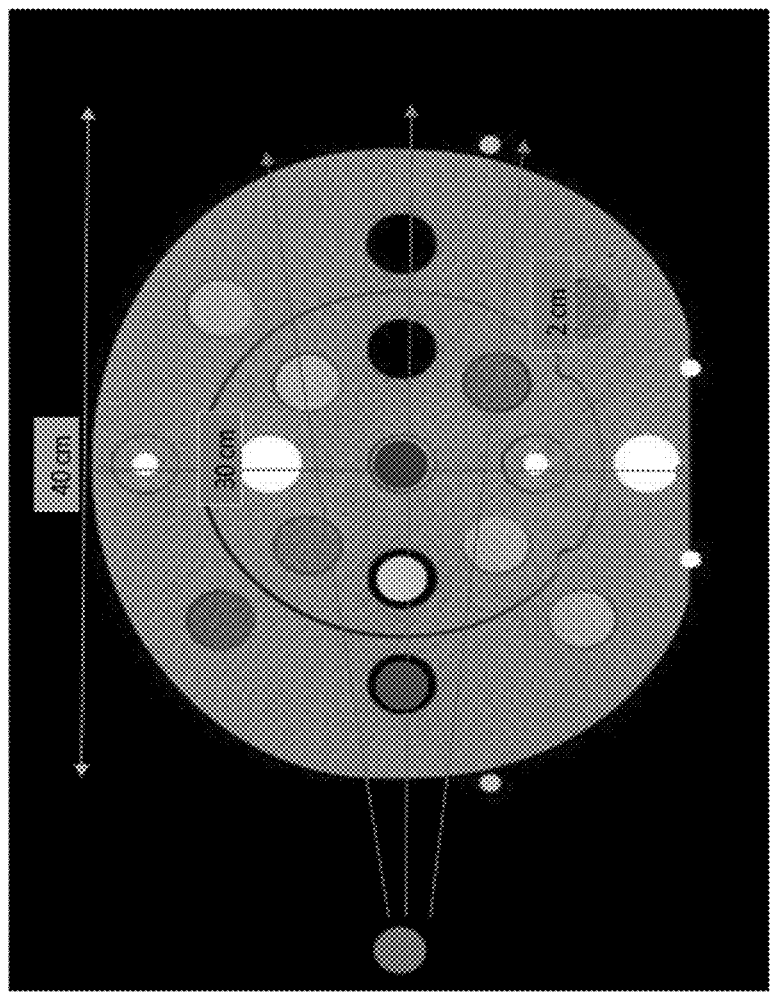
FIG. 40 is an axial CT image of a Gammex Advanced Electron Density phantom (left panel) and a table showing distances of the central beam.
Figures 41, 42:
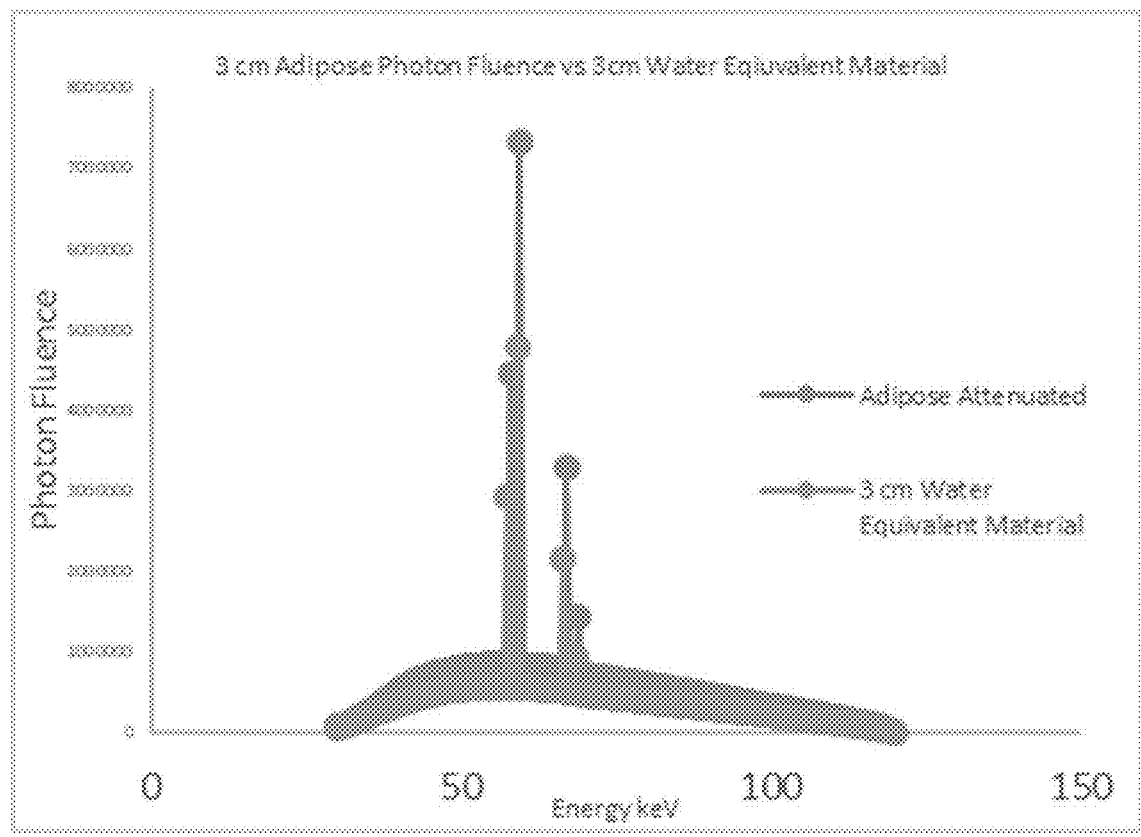
FIG. 41 is a graph comparing photon fluence in 3 cm adipose and 3 cm water equivalent material.
FIG. 42 is a table showing average energy (keV) for 3 cm of adipose and 3 cm water equivalent material.

The same finite element analysis was completed for a commercially available phantom manufactured by Gammex. FIG. 40 illustrates an axial CT image of the Gammex Advanced Electron Density phantom. The phantom is constructed as a 40 cm ellipsoid made of water equivalent materials with 17 inserts for materials of varying electron density (inserts are 2.8 cm in diameter). In the analysis of beam hardening for this phantom a central beam path was utilized. The geometry of this phantom mimics an abdomen, but the geometric configuration of the materials does not match the configuration in a clinical setting. Thus, the relative attenuation of the poly energetic radiation beam does not match what is observed in a clinical setting. When comparing the first 3 cm of the phantom of the present disclosure compared to the Gammex phantom, a variation in the attenuated beam fluence can be seen in the 40 to 80 keV energy range, as shown in FIGS. 41-42.

Figures 43, 44:
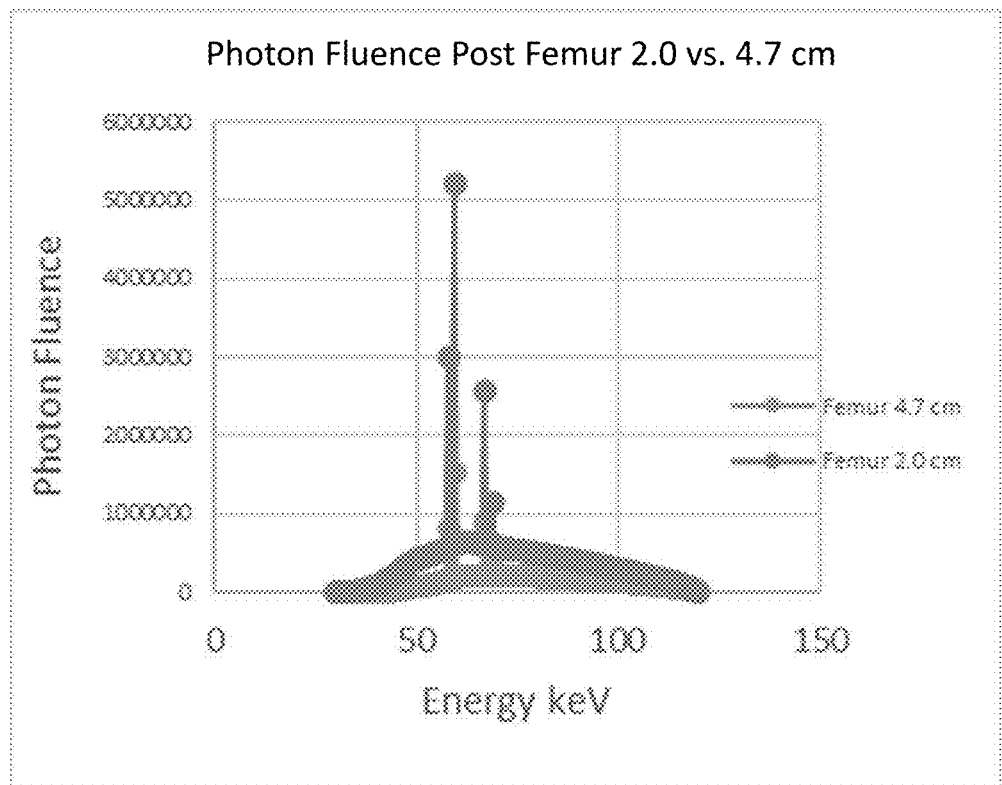
FIG. 43 is a graph showing photon fluence post femoral head insert having a diameter of 2.0 cm (Gammex) vs. 4.7 cm.
FIG. 44 is a table showing average energy variation (keV) of the Gammex compared to a phantom according to one or more embodiments of the disclosure.

The variation in the average energy is minimal due to the relative similarity in water and adipose in attenuation coefficient. The larger variation occurs after the femoral head where the attenuation coefficient is vastly different than water or any other tissue mimicking insert. The Gammex phantom does not have a fixed geometry, so the user can place inserts in any configuration. If this configuration does not mimic the anatomic configuration as seen in patients, there will be a large variation in the measured in the measured electron density. The electron density inserts do not mimic the size of the anatomy in the patient. Discrete element analysis was done to analyze the average energy and spectral change based on the femoral insert size of the Gammex phantom versus the presently disclosed phantom. The Gammex phantom has a femoral head insert size of 2.0 cm and the presently disclosed phantom has femoral head size of 4.7 cm in diameter. Based on this analysis the average energy variation is 5 keV between the two. This variation propagates over entire phantom, leading to large variations in the measurement of electron density. See FIGS. 43-44.

Impact on HU Measurements

Material composition and shape of the electron density phantom matter to measuring Hounsfield Units, but the spatial location of the material within the phantom impacts the measurement of Hounsfield Units as well. The degree of beam hardening will be different based on the type of material and the amount of that material with which the poly energetic beam interacts. When a poly energetic beam interacts with fat, less attenuation with low energy photons occurs as compared to muscle or bone. This applies to both a phantom and a clinical scan. Commercially available electron density phantoms do not consider the beam hardening relative to material position because they are typically designed with a base phantom material that is equivalent to water, and geometrically uniform. This uniformity does not take into context the lack of uniformity of human anatomy. Hounsfield Units are tabulated based on material attenuation coefficient and the energy (average energy) of the radiation beam. If the radiation beam attenuation for the phantom compared to the clinical setting is different, then the Hounsfield Units will vary significantly. The demonstration of beam hardening through the finite element analysis highlights the improvement of the presently disclosed phantom over other phantoms known in the field.

In one embodiment, calibration phantom for radiometric characterization and/or radiotherapy dose calculation of a subject is provided, comprising: an ellipsoid base having a primary volume defining a plurality of cylindrical voids, each of said cylindrical voids configured to receive a cylindrical insert having a diameter, wherein the ellipsoid base, the primary volume, and each of said inserts are formed from a tissue substitution material independently selected to approximate a radiological property of an anatomical feature of the subject to which the ellipsoid base, the primary volume, and each of said inserts corresponds, wherein the radiological property of the tissue substitution material, the diameter of each of said inserts, and a location of each of said inserts within the ellipsoid base are selected to mimic beam hardening upon exposure of the calibration phantom to a radiation beam.

The diameter of the ellipsoid base may vary, depending on the anatomy to which the phantom is designed to correspond. In a specific embodiment, the phantom approximates a human pelvis, having a diameter of from about 30 to about 40 cm. In a specific embodiment, the transverse diameter of the ellipsoid base is about 33 cm.

In another embodiment, the calibration phantom further comprises one or more peripheral rings disposed concentrically about the ellipsoid base, wherein the one or more peripheral rings are formed from a tissue substitution material independently selected to approximate a radiological property of an anatomical feature of the subject to which the one or more peripheral rings correspond.

The thickness of the one or more peripheral rings may be selected to correspond to the anatomy to which the phantom is designed to correspond. In embodiments, a peripheral ring thickness may range from about 1 cm to about 5 cm, or about 1 cm, about 2 cm, about 3 cm, about 4 cm, or about 5 cm.

In embodiments, the radiological property of a tissue substitution material is selected from the group consisting of density, electron density, mass attenuation coefficient, linear attenuation coefficient, stopping power, and combinations thereof.

The calibration phantoms disclosed herein comprise a morphology that is designed to accurately model a human body or a portion thereof. In embodiments, the location of each of said inserts within the calibration phantom is selected to mimic anthropomorphic and/or anthropometric characteristics of a human subject. In embodiments, the distribution of the inserts provides a calibration phantom that mimics the anthropomorphic and/or anthropometric characteristics of a head, neck, torso, chest, arm, leg, pelvis, or body of a human subject.

In a specific embodiment, the calibration phantom models a human pelvis, and more specifically a human male pelvis for use in radiotherapy for prostate cancer. In such an embodiment, two of the inserts are femoral head inserts, wherein the diameter and tissue substitution material of each of said femoral head inserts are selected to mimic the radiological properties of a femoral head of the pelvis of the human subject. Optionally, the femoral head inserts are removable. In a specific embodiment, the femoral head inserts are optionally configured to comprise one or more additional removable inserts selected to mimic bone tissue.

The calibration phantom described herein comprises tissue substitution materials that are independently selected to mimic a human form. In embodiments, the tissue substitution materials are selected to mimic beam hardening of a radiation beam. In specific embodiments, the tissue substitution materials comprise polyurethanes, the polyurethanes comprising additives that confer radiological properties that mimic features of the human body. In more specific embodiments, the tissue substitution materials comprise a polyurethane base material comprising additives selected from and LiOH, $CaCO_3$, and Teflon®.

In embodiments, each of the cylindrical inserts of the one or more peripheral rings is formed from a tissue substitution material independently selected to mimic a body tissue selected from muscle and adipose.

Advantageously, the calibration phantom described herein is customizable to mimic the anthropomorphic and anthropometric characteristics of a specific patient or patient group. In embodiments, the patient group is defined by a common characteristic selected from sex, age, height, weight, race, ethnicity, and combinations thereof. In embodiments, the calibration phantom is customizable to provide a patient-specific model for use in personalized medicine.

The calibration phantom may comprise inserts of various diameters and tissue substitution materials. In embodiments, the diameter of an insert ranges from about 2 cm to about 8 cm, or about 2 cm, about 3 cm, about 4 cm, about 5 cm, about 6 cm, about 7 cm, or about 8 cm. In a specific embodiment, an insert representing a femoral head comprises a diameter of about 4.7 cm, or about 5 cm.

The physical geometry, or layout, of the calibration phantoms describe herein include a plurality of volumes and inserts. In embodiments, a calibration phantom of the present disclosure comprises 0, 1, 2, 4, 5, 6, 7, 8, 9, 10, 11, 12, or more inserts within the ellipsoid base. In a very specific embodiment, the calibration phantom comprises a central ellipsoid base comprising 10 or 11 central inserts, each selected to anthropometrically and anthropomorphically model the human body or a portion thereof.

In embodiments, the calibration phantom further comprises a second peripheral ring disposed concentrically about the first peripheral ring, the second peripheral ring optionally comprising a plurality of removable peripheral inserts. In a specific embodiment, the first peripheral ring comprises 0, 1, 2, 3, or 4 peripheral inserts. In embodiments, the first and second peripheral rings each comprise 0, 1, 2, 3, or 4 peripheral inserts. In a more specific embodiment, each of the first and second peripheral rings comprises 4 peripheral inserts.

The inserts of the ellipsoidal base and peripheral ring(s) are each formed from a tissue substitution material independently selected to mimic a body tissue. In embodiments, the body tissue is selected from the group consisting of lung, breast, liver, brain, bone, thyroid, prostate, rectum, bladder, water, air, adipose, muscle, and the like.

In a specific embodiment, each of the inserts is formed from a tissue substitution material independently selected to mimic a body tissue selected from bone, water, air, and muscle. In a specific embodiment, each of the inserts of peripheral rings are formed from a tissue substitution material independently selected to mimic a body tissue selected from muscle and adipose.

In another embodiment, a method of mitigating off-target exposure to radiotherapy in a subject in need thereof is provided, the method comprising calibrating a radiation-generating therapeutic device using a calibration phantom according to any of the embodiments disclosed herein, prior to administering the radiotherapy to the subject. Exemplary methods of radiotherapy includes both proton beam therapy and conventional external beam radiation.

In another embodiment, a method of improving certainty of a radiotherapeutic dose delivered to a human subject is provided, the method comprising calibrating a radiation-generating therapeutic device using the calibration phantom according to any of the embodiments disclosed herein, prior to administering the radiotherapeutic dose to the human subject.

In another embodiment, a method of calibrating a radiation-generating device is provided, the method comprising (a) imaging a calibration phantom according to any of the embodiments disclosed herein via computed tomography (CT) to provide a CT image; (b) measuring electron density of the calibration phantom; (c) determining Hounsfield Units of the calibration phantom; and (d) comparing the Hounsfield Units against the known electron density.

Patents, applications, and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A calibration phantom for radiometric characterization and/or radiotherapy dose calculation of a subject, comprising:
    an ellipsoid base having a primary volume defining a plurality of cylindrical voids, each of said cylindrical voids configured to receive a cylindrical insert having a diameter, wherein the ellipsoid base, the primary volume, and each of said inserts are formed from a tissue substitution material independently selected to approximate a radiological property of an anatomical feature of the subject to which the ellipsoid base, the primary volume, and each of said inserts corresponds,
    wherein the radiological property of the tissue substitution material, the diameter of each of said inserts, and a location of each of said inserts within the ellipsoid base are selected to mimic beam hardening upon exposure of the calibration phantom to a radiation beam; and
    wherein the location of each of said inserts is selected to mimic the anthropomorphic and/or anthropometric characteristics of a head, neck, torso, chest, arm, leg, pelvis, or body of the subject.

2. The calibration phantom according to claim 1, further comprising:
    one or more peripheral rings disposed concentrically about the ellipsoid base,
    wherein the one or more peripheral rings are formed from a tissue substitution material independently selected to approximate a radiological property of an anatomical feature of the subject to which the one or more peripheral rings correspond.

3. The calibration phantom according to claim 2, wherein the one or more peripheral rings have a peripheral volume defining one or more cylindrical voids, each of said cylindrical voids configured to receive a cylindrical insert, wherein each of said inserts is formed from a tissue substitution material independently selected to approximate a radiological property of an anatomical feature of the subject to which each of said inserts corresponds.

4. The calibration phantom according to claim 2, wherein the radiological property is selected from the group consisting of density, electron density, mass attenuation coefficient, linear attenuation coefficient, stopping power, and combinations thereof.

5. The calibration phantom according to claim 1, wherein the calibration phantom mimics the anthropomorphic and anthropometric characteristics of a pelvis of the human subject.

6. The calibration phantom according to claim 1, wherein two of said inserts are femoral head inserts, wherein the diameter and tissue substitution material of each of said femoral head inserts are selected to mimic the radiological properties of a femoral head of the pelvis of the human subject.

7. The calibration phantom according to claim 6, wherein the femoral head inserts are removable.

8. The calibration phantom according to claim 2, wherein the one or more peripheral rings are formed from a tissue substitution material selected to mimic adipose or muscle.

9. The calibration phantom according to claim 2, wherein the inserts are each formed from a tissue substitution material independently selected to mimic a body tissue selected from lung, breast, liver, brain, bone, thyroid, water, air, adipose, muscle, or combinations thereof.

10. The calibration phantom according to claim 6, wherein the two inserts that mimic the radiological properties of the femoral head of the pelvis are configured to receive one or more cylindrical inserts that mimic bone.

11. The calibration phantom according to claim 3, wherein each of the cylindrical inserts of the one or more peripheral rings is formed from a tissue substitution material independently selected to mimic a body tissue selected from muscle and adipose.

12. The calibration phantom according to claim 1, wherein the calibration phantom is customizable to mimic the anthropomorphic and anthropometric characteristics of a specific patient or patient group.

13. The calibration phantom according to claim 12, wherein the patient group is defined by a common characteristic selected from sex, age, height, weight, race, ethnicity, and combinations thereof.

14. The calibration phantom according to claim 3, wherein the diameter of each of said inserts ranges from about 2 cm to about 8 cm.

15. The calibration phantom according to claim 7, wherein the femoral head inserts each comprise a diameter of about 4.7 cm.

16. A method of mitigating off-target exposure to radiotherapy in a subject in need thereof, the method comprising calibrating a radiation-generating therapeutic device using the calibration phantom according to claim 1 prior to administering the radiotherapy to the subject.

17. The method according to claim 16, wherein the radiotherapy is selected from proton beam therapy and conventional external beam radiation.

18. A method of improving certainty of a radiotherapeutic dose delivered to a human subject, the method comprising calibrating a radiation-generating therapeutic device using the calibration phantom according to claim 1 prior to administering the radiotherapeutic dose to the human subject.

* * * * *